United States Patent [19]
Jones et al.

[11] Patent Number: 5,920,000
[45] Date of Patent: Jul. 6, 1999

[54] PLANT PATHOGEN RESISTANCE GENES AND USES THEREOF

[75] Inventors: Jonathan D. G. Jones; Kim E. Hammond-Kosack; Colwyn M. Thomas; David A. Jones, all of Norwich, United Kingdom

[73] Assignee: Plant Bioscience Limited, Norwich, United Kingdom

[21] Appl. No.: 08/666,271

[22] PCT Filed: Dec. 23, 1994

[86] PCT No.: PCT/GB94/02812

§ 371 Date: Sep. 19, 1996

§ 102(e) Date: Sep. 19, 1996

[87] PCT Pub. No.: WO95/18230

PCT Pub. Date: Jul. 6, 1995

[30] Foreign Application Priority Data

Dec. 24, 1993 [GB] United Kingdom .................... 9326428
May 11, 1994 [GB] United Kingdom .................... 9409363

[51] Int. Cl.$^6$ .............................. C12N 5/00; C12N 15/00
[52] U.S. Cl. ........................ 800/301; 800/279; 800/295; 435/6; 435/91.1; 435/252.3; 435/254.11; 435/320.1; 435/419; 436/94; 536/23.6; 935/9; 935/64; 935/67
[58] Field of Search ............................. 435/320.1, 172.3, 435/411, 419, 418, 252.3, 254.11, 6; 536/23.6; 800/205, 250, DIG. 44; 935/9, 64, 67; 436/94

[56] References Cited

FOREIGN PATENT DOCUMENTS

WO 91/15585  10/1991  WIPO .
WO93/11241   6/1993  WIPO .

OTHER PUBLICATIONS

JD Watson et al (1987) Molecular Biology of the Gene p. 313.

KE Hammond–Kosack et al (1994) Plant Cell 6:361–374.

Toubart et al, "Cloning and characterization of the gene encoding the endopolygalacturonase–inhibiting protein (PGIP) of *Phaseolus vulgaris* L.", The Plant Journal 2(3):367–373 (1992).

Stotz et al, "Molecular Characterization of a Polygalacturonase Inhibitor from *Pyrus communis* L. cv Bartlett", Plant Physiol 102:133–138 (1993).

Jones et al, "Isolation of the Tomato Cf–9 Gene for Resistance to *Cladosporium fulvum* by Transposon Tagging", Science 266:789–793 (1994).

Jones et al, "Two Complex Resistance Loci Revealed in Tomato by Classical and RFLP Mapping of the Cf–2, Cf–4, Cf–5, and Cf–9 Genes for Resistance to *Cladosporium fulvum*", Molecular Plant–Microbe Interactions 6(3):348–357 (1993).

Dickinson et al, "Strategies for the Cloning of Genes in Tomato for Resistance to *Fulvia fulva*", Advances in Molecular Genetics of Plant–Microbe Interactions 1:276–279 (1991).

Bennetzen et al, "Approaches and Progress in the Molecular Cloning for Plant Disease Resistance Genes", Genetic Engineering 14:99–124 (1992).

Martin et al, "Map–Based Cloning of a Protein Kinase Gene Conferring Disease Resistance in Tomato", Science 262:1432–1436 (1993).

Johal et al, "Reductase Activity Encoded by the HM1 Disease Resistance Gene in Maize", Science 258:985–987 (1992).

*Primary Examiner*—Bruce R. Campell
*Attorney, Agent, or Firm*—Nixon & Vanderhye PC

[57] ABSTRACT

The present invention relates to pathogen resistance in plants, and identification and use of pathogen resistance genes.

23 Claims, 7 Drawing Sheets

FIGURE 2

```
   1  CATAGTCTTT GCATATTTGG ATTAAACAGG GGCATTATTG AACCAAACTA
  51  TTAGATGTAT GAAAATTTTG ACCAAGCTA TTGACAACAC GAACATTTTT
 101  AGACCAAACT ATTAACTCAG AATATTTTCC GTTGAATGAA TAAGGTAACT
 151  AGTAGTAAAT TTTTAGACCA AACTATGAAG AACATGCCAT GTCTGGACTC
 201  CTGCACTATC TTCCATCAAC AGGTCAATTC TCTCAACTCT ATTGGTGGAA
 251  GGTAGACGGT ACAAATTGAA TTATATTAAA AGACAAGCTC ACCTGAGCAT
 301  CACTGTTATA CAACAACAAC AAACTACGCT TCAGCCCCAA ACAATAGTGA
 351  CCCGAATCAT ATATTGTCAC GAGTTTTTT TAGAGTATGT TGCATATATT
 401  ATACTCAACT TAGGGTTTGT CATTCTGATG CTTCGTACAA ATTTATTGAA
 451  TTTTCAACTT TAAAGGTTTA TGAACCAAAT ATTACGCTTA CTATGATAGC
 501  GGTCTTTTTT GATTAATCAA ACTTATTGAA TTTTCAACTT TAAAGGTTTT
 551  TCCCCGTTCT ATACACAAAC TAAGAAAAAT TTAAATTATA TAGTCTTTGG
 601  ATGGTGACCT ATTTGGATGG TAACATTATT GGACCAAACT ATTGATAACG
 651  CGGACATTGT TAGACCAAAC TGAGAAGGAC ATGTCTGGAC TCCTGCTCCG
 701  TCTTCCATCA GCAGGTCGAT TCTTGTGGAA AATTAGCTCG AGGTGGCGCA
 751  CTATGTGAGG TAACTAGTAC TAAATTTTTC TTTGCTTAAT TTGTGCTATA
 801  TATACCTCAT CTAAATTATT GAATAGTCAC ACAAAGCAAA CATTTCTTGA
 851  TTTCTTCTCT ATCAACATAA CAAGTTTTGA TCATTTTTAG TGCAGAAATG
 901  GATTGTGTAA AACTTGTATT CCTTATGCTA TATACCTTTC TCTGTCAACT
 951  TGCTTTATCC TCATCCTTGC CTCATTTGTG CCCCGAAGAT CAAGCTCTTT
1001  CTCTTCTACA ATTCAAGAAC ATGTTTACCA TTAATCCTAA TGCTTCTGAT
1051  TATTGTTACG ACATAAGAAC ATACGTAGAC ATTCAGTCAT ATCCAAGAAC
1101  TCTTTCTTGG AACAAAAGCA CAAGTTGCTG CTCATGGGAT GGCGTTCATT
1151  GTGACGAGAC GACAGGACAA GTGATTGCGC TTGACCTCCG TTGCAGCCAA
1201  CTTCAAGGCA AGTTTCATTC AATAGTAGC CTCTTTCAAC TCTCCAATCT
1251  CAAAAGGCTT GATTTGTCTT TTAATAATTT CACTGGATCA CTCATTTCAC
1301  CAAAATTTGG TGAGTTTTCA AATTTGACGC ATCTCGATTT GTCGCATTCT
1351  AGTTTTACAG GTCTAATTCC TTCTGAAATC TGTCACCTTT CTAAACTACA
1401  CGTTCTTCGT ATATGTGATC AATATGGGCT TAGTCTTGTA CCTTACAATT
```

FIGURE 2 CONTINUED

```
1451 TTGAACTGCT CCTTAAGAAC TTGACCCAAT TAAGAGAGCT CAACCTTGAA
1501 TCTGTAAACA TCTCTTCCAC TATTCCTTCA AATTTCTCTT CTCATTTAAC
1551 AACTCTACAA CTTTCAGGCA CAGAGTTACA TGGGATATTG CCCGAAAGAG
1601 TTTTTCACCT TTCCAACTTA CAATCCCTTC ATTTATCAGT CAATCCCCAG
1651 CTCACGGTTA GGTTTCCCAC AACCAAATGG AATAGCAGTG CATCACTCAT
1701 GACGTTATAC GTCGATAGTG TGAATATTGC TGATAGGATA CCTAAATCAT
1751 TTAGCCATCT AACTTCACTT CATGAGTTGT ACATGGGTCG TTGTAATCTG
1801 TCAGGGCCTA TTCCTAAACC TCTATGGAAT CTCACCAACA TAGTGTTTTT
1851 GCACCTTGGT GATAACCATC TTGAAGGACC AATTTCCCAT TTCACGATAT
1901 TTGAAAAGCT CAAGAGGTTA TCACTTGTAA ATAACAACTT TGATGGCGGA
1951 CTTGAGTTCT TATCCTTTAA CACCCAACTT GAACGGCTAG ATTTATCATC
2001 CAATTCCCTA ACTGGTCCAA TTCCATCCAA CATAAGCGGA CTTCAAAACC
2051 TAGAATGTCT CTACTTGTCA TCAAACCACT TGAATGGGAG TATACCTTCC
2101 TGGATATTCT CCCTTCCTTC ACTGGTTGAG TTAGACTTGA GCAATAACAC
2151 TTTCAGTGGA AAAATTCAAG AGTTCAAGTC CAAAACATTA AGTGCCGTTA
2201 CTCTAAAACA AAATAAGCTG AAAGGTCGTA TTCCGAATTC ACTCCTAAAC
2251 CAGAAGAACC TACAATTACT TCTCCTTTCA CACAATAATA TCAGTGGACA
2301 TATTTCTTCA GCTATCTGCA ATCTGAAAAC ATTGATATTG TTAGACTTGG
2351 GAAGTAATAA TTTGGAGGGA ACAATCCCAC AATGCGTGGT TGAGAGGAAC
2401 GAATACCTTT CGCATTTGGA TTTGAGCAAA AACAGACTTA GTGGGACAAT
2451 CAATACAACT TTTAGTGTTG GAAACATTTT AAGGGTCATT AGCTTGCACG
2501 GGAATAAGCT AACGGGGAAA GTCCCACGAT CTATGATCAA TTGCAAGTAT
2551 TTGACACTAC TTGATCTAGG TAACAATATG TTGAATGACA CATTTCCAAA
2601 CTGGTTGGGA TACCTATTTC AATTGAAGAT TTTAAGCTTG AGATCAAATA
2651 AGTTGCATGG TCCCATCAAA TCTTCAGGGA ATACAAACTT GTTTATGGGT
2701 CTTCAAATTC TTGATCTATC ATCTAATGGA TTTAGTGGGA ATTTACCCGA
2751 AAGAATTTTG GGGAATTTGC AAACCATGAA GGAAATTGAT GAGAGTACAG
2801 GATTCCCAGA GTATATTTCT GATCCATATG ATATTATTA CAATTATTTG
2851 ACGACAATTT CTACAAAGGG ACAAGATTAT GATTCTGTTC GAATTTTGGA
2901 TTCTAACATG ATTATCAATC TCTCAAAGAA CAGATTTGAA GGTCATATTC
```

FIGURE 2 CONTINUED

```
2951  CAAGCATTAT  TGGAGATCTT  GTTGGACTTC  GTACGTTGAA  CTTGTCTCAC
3001  AATGTCTTGG  AAGGTCATAT  ACCGGCATCA  TTTCAAAATT  TATCAGTACT
3051  CGAATCTTTG  GATCTCTCAT  CTAATAAAAT  CAGCGGAGAA  ATTCCGCAGC
3101  AGCTTGCATC  CCTCACATTC  CTTGAAGTCT  TAAATCTCTC  TCACAATCAT
3151  CTTGTTGGAT  GCATCCCCAA  AGGAAAACAA  TTTGATTCGT  TCGGGAACAC
3201  TTCGTACCAA  GGGAATGATG  GGTTACGCGG  ATTTCCACTC  TCAAAACTTT
3251  GTGGTGGTGA  AGATCAAGTG  ACAACTCCAG  CTGAGCTAGA  TCAAGAAGAG
3301  GAGGAAGAAG  ATTCACCAAT  GATCAGTTGG  CAGGGGGTTC  TCGTGGGTTA
3351  CGGTTGTGGA  CTTGTTATTG  GACTGTCCGT  AATATACATA  ATGTGGTCAA
3401  CTCAATATCC  AGCATGGTTT  TCGAGGATGG  ATTTAAAGTT  GGAACACATA
3451  ATTACTACGA  AAATGAAAAA  GCACAAGAAA  AGATATTAGT  GAGTAGCTAT
3501  ACCTCCAGGT  ATTCCACTTG  ATCATTATCT  TTCAGAAGAT  TATTTTTTGT
3551  ATATCGATGA  AATTATCGAC  CTCCTTCATC  CTCAAAGCTC  TTAACTTTCA
3601  CTCTTCATTT  TTGAAAATTT  CAGGATTCAA  AGATTTCCGA  GTTCCCAGTT
3651  GCTTGGGATG  CAGATAAAAG  CCTTTTTATC  TTTCATAGTT  TCTTATCCTA
3701  TGAATAAAGA  TTTTATTTTC  ATTTGTCTAT  GGCACGTAGA  TATGTTCCGT
3751  CACTAAAAAC  ATTGTATTTC  TCTCAACTCT  TTCGTCACAT  GATATCAAAG
3801  AACACTTGAC  TTCAATTAAG  TTACTGTAGT  CTGCTATTTT  AATTTTTTCC
3851  ATTGAAACAC  AACTGACGTA  TCTTGAGAAA  GAGACTATGA  TCCCCCGGGC
3901  TGCAG
```

FIGURE 3

```
  1   MDCVKLVFLM  LYTFLCQLAL  SSSLPHLCPE  DQALSLLQFK  NMFTINPNAS
 51   DYCYDIRTYV  DIQSYPRTLS  WNKSTSCCSW  DGVHCDETTG  QVIALDLRCS
101   QLQGKFHSNS  SLFQLSNLKR  LDLSFNNFTG  SLISPKFGEF  SNLTHLDLSH
151   SSFTGLIPSE  ICHLSKLHVL  RICDQYGLSL  VPYNFELLLK  NLTQLRELNL
201   ESVNISSTIP  SNFSSHLTTL  QLSGTELHGI  LPERVFHLSN  LQSLHLSVNP
251   QLTVRFPTTK  WNSSASLMTL  YVDSVNIADR  IPKSFSHLTS  LHELYMGRCN
301   LSGPIPKPLW  NLTNIVFLHL  GDNHLEGPIS  HFTIFEKLKR  LSLVNNNFDG
351   GLEFLSFNTQ  LERLDLSSNS  LTGPIPSNIS  GLQNLECLYL  SSNHLNGSIP
401   SWIFSLPSLV  ELDLSNNTFS  GKIQEFKSKT  LSAVTLKQNK  LKGRIPNSLL
451   NQKNLQLLLL  SHNNISGHIS  SAICNLKTLI  LLDLGSNNLE  GTIPQCVVER
```

FIGURE 3 CONTINUED

```
501  NEYLSHLDLS  KNRLSGTINT  TFSVGNILRV  ISLHGNKLTG  KVPRSMINCK
551  YLTLLDLGNN  MLNDTFPNWL  GYLFQLKILS  LRSNKLHGPI  KSSGNTNLFM
601  GLQILDLSSN  GFSGNLPERI  LGNLQTMKEI  DESTGFPEYI  SDPYDIYYNY
651  LTTISTKGQD  YDSVRILDSN  MIINLSKNRF  EGHIPSIIGD  LVGLRTLNLS
701  HNVLEGHIPA  SFQNLSVLES  LDLSSNKISG  EIPQQLASLT  FLEVLNLSHN
751  HLVGCIPKGK  QFDSFGNTSY  QGNDGLRGFP  LSKLCGGEDQ  VTTPAELDQE
801  EEEEDSPMIS  WQGVLVGYGC  GLVIGLSVIY  IMWSTQYPAW  FSRMDLKLEH
851  IITTKMKKHK  KRY
```

FIGURE 4

```
1    CATTTCTTGA  TTTCTTCTCT  ATCAACATAA  CAAGTTTTGA  TCATTTTTAG
51   TGCAGAAATG  GATTGTGTAA  AACTTGTATT  CCTTATGCTA  TATACCTTTC
101  TCTGTCAACT  TGCTTTATCC  TCATCCTTGC  CTCATTTGTG  CCCCGAAGAT
151  CAAGCTCTTT  CTCTTCTACA  ATTCAAGAAC  ATGTTTACCA  TTAATCCTAA
201  TGCTTCTGAT  TATTGTTACG  ACATAAGAAC  ATACGTAGAC  ATTCAGTCAT
251  ATCCAAGAAC  TCTTTCTTGG  AACAAAAGCA  CAAGTTGCTG  CTCATGGGAT
301  GGCGTTCATT  GTGACGAGAC  GACAGGACAA  GTGATTGCGC  TTGACCTCCG
351  TTGCAGCCAA  CTTCAAGGCA  AGTTTCATTC  AATAGTAGC   CTCTTTCAAC
401  TCTCCAATCT  CAAAAGGCTT  GATTTGTCTT  TTAATAATTT  CACTGGATCA
451  CTCATTTCAC  CAAAATTTGG  TGAGTTTTCA  AATTTGACGC  ATCTCGATTT
501  GTCGCATTCT  AGTTTTACAG  GTCTAATTCC  TTCTGAAATC  TGTCACCTTT
551  CTAAACTACA  CGTTCTTCGT  ATATGTGATC  AATATGGGCT  TAGTCTTGTA
601  CCTTACAATT  TTGAACTGCT  CCTTAAGAAC  TTGACCCAAT  TAAGAGAGCT
651  CAACCTTGAA  TCTGTAAACA  TCTCTTCCAC  TATTCCTTCA  AATTTCTCTT
701  CTCATTTAAC  AACTCTACAA  CTTTCAGGCA  CAGAGTTACA  TGGGATATTG
751  CCCGAAAGAG  TTTTTCACCT  TTCCAACTTA  CAATCCCTTC  ATTTATCAGT
801  CAATCCCCAG  CTCACGGTTA  GGTTTCCCAC  AACCAAATGG  AATAGCAGTG
851  CATCACTCAT  GACGTTATAC  GTCGATAGTG  TGAATATTGC  TGATAGGATA
901  CCTAAATCAT  TTAGCCATCT  AACTTCACTT  CATGAGTTGT  ACATGGGTCG
951  TTGTAATCTG  TCAGGGCCTA  TTCCTAAACC  TCTATGGAAT  CTCACCAACA
```

FIGURE 4 CONTINUED

```
1001 TAGTGTTTTT GCACCTTGGT GATAACCATC TTGAAGGACC AATTTCCCAT
1051 TTCACGATAT TTGAAAAGCT CAAGAGGTTA TCACTTGTAA ATAACAACTT
1101 TGATGGCGGA CTTGAGTTCT TATCCTTTAA CACCCAACTT GAACGGCTAG
1151 ATTTATCATC CAATTCCCTA ACTGGTCCAA TTCCATCCAA CATAAGCGGA
1201 CTTCAAAACC TAGAATGTCT CTACTTGTCA TCAAACCACT TGAATGGGAG
1251 TATACCTTCC TGGATATTCT CCCTTCCTTC ACTGGTTGAG TTAGACTTGA
1301 GCAATAACAC TTTCAGTGGA AAAATTCAAG AGTTCAAGTC CAAAACATTA
1351 AGTGCCGTTA CTCTAAAACA AAATAAGCTG AAAGGTCGTA TTCCGAATTC
1401 ACTCCTAAAC CAGAAGAACC TACAATTACT TCTCCTTTCA CACAATAATA
1451 TCAGTGGACA TATTTCTTCA GCTATCTGCA ATCTGAAAAC ATTGATATTG
1501 TTAGACTTGG GAAGTAATAA TTTGGAGGGA ACAATCCCAC AATGCGTGGT
1551 TGAGAGGAAC GAATACCTTT CGCATTTGGA TTTGAGCAAA AACAGACTTA
1601 GTGGGACAAT CAATACAACT TTTAGTGTTG GAAACATTTT AAGGGTCATT
1651 AGCTTGCACG GGAATAAGCT AACGGGGAAA GTCCCACGAT CTATGATCAA
1701 TTGCAAGTAT TTGACACTAC TTGATCTAGG TAACAATATG TTGAATGACA
1751 CATTTCCAAA CTGGTTGGGA TACCTATTTC AATTGAAGAT TTTAAGCTTG
1801 AGATCAAATA AGTTGCATGG TCCCATCAAA TCTTCAGGGA ATACAAACTT
1851 GTTTATGGGT CTTCAAATTC TTGATCTATC ATCTAATGGA TTTAGTGGGA
1901 ATTTACCCGA AAGAATTTTG GGGAATTTGC AAACCATGAA GGAAATTGAT
1951 GAGAGTACAG GATTCCCAGA GTATATTTCT GATCCATATG ATATTTATTA
2001 CAATTATTTG ACGACAATTT CTACAAAGGG ACAAGATTAT GATTCTGTTC
2051 GAATTTTGGA TTCTAACATG ATTATCAATC TCTCAAAGAA CAGATTTGAA
2101 GGTCATATTC CAAGCATTAT TGGAGATCTT GTTGGACTTC GTACGTTGAA
2151 CTTGTCTCAC AATGTCTTGG AAGGTCATAT ACCGGCATCA TTTCAAAATT
2201 TATCAGTACT CGAATCTTTG GATCTCTCAT CTAATAAAAT CAGCGGAGAA
2251 ATTCCGCAGC AGCTTGCATC CCTCACATTC CTTGAAGTCT TAAATCTCTC
2301 TCACAATCAT CTTGTTGGAT GCATCCCCAA AGGAAAACAA TTTGATTCGT
2351 TCGGGAACAC TTCGTACCAA GGGAATGATG GGTTACGCGG ATTTCCACTC
2401 TCAAAACTTT GTGGTGGTGA AGATCAAGTG ACAACTCCAG CTGAGCTAGA
```

FIGURE 4 CONTINUED

```
2451 TCAAGAAGAG GAGGAAGAAG ATTCACCAAT GATCAGTTGG CAGGGGGTTC
2501 TCGTGGGTTA CGGTTGTGGA CTTGTTATTG GACTGTCCGT AATATACATA
2551 ATGTGGTCAA CTCAATATCC AGCATGGTTT TCGAGGATGG ATTTAAAGTT
2601 GGAACACATA ATTACTACGA AAATGAAAAA GCACAAGAAA AGATATTAGT
2651 GAGTAGCTAT ACCTCCAGGA TTCAAAGATT TCCGAGTTCC CAGTTGCTTG
2701 GGATGCAGAT AAAAGCCTTT TTATCTTTCA TAGTTTCTTA TCCTATGAAT
2751 AAAGATTTTA TTTTCATTTG TCTATGGCAC GTAGATATGT TCCGTCACTA
2801 AAAACATTGT ATTTCTCTCA ACTCTTTCGT CACATGATAT CAAAGAACAC
2851 TTGACTTCAA TTAAGTTAAA AAAAAAAAA
```

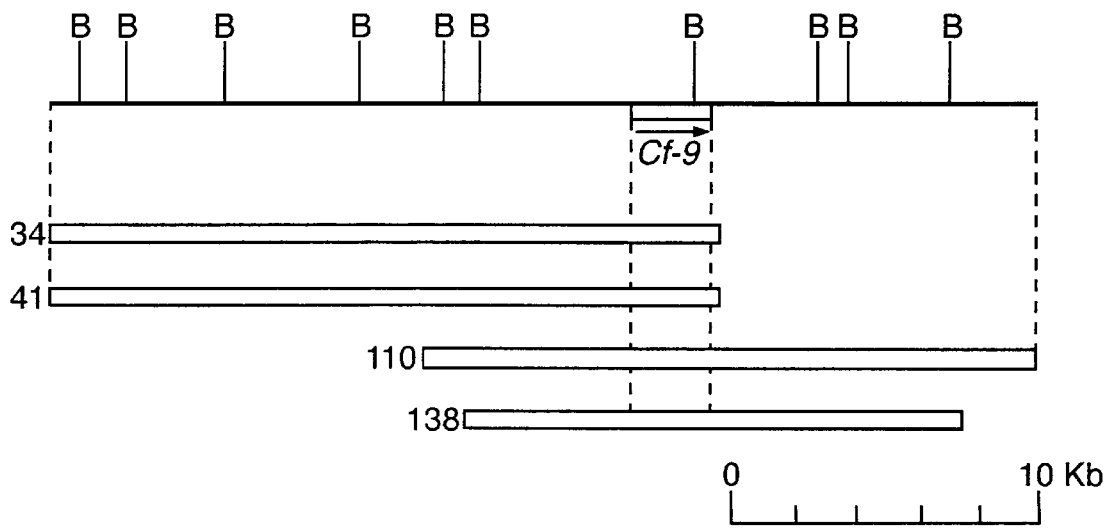

FIGURE 5

PLANT PATHOGEN RESISTANCE GENES AND USES THEREOF

The present invention relates to pathogen resistance in plants and more particularly the identification and use of pathogen resistance genes.

Plants are constantly challenged by potentially pathogenic microorganisms. Crop plants are particularly vulnerable, because they are usually grown as genetically uniform monocultures; when disease strikes, losses can be severe. However, most plants are resistant to most plant pathogens. To defend themselves, plants have evolved an array of both preexisting and inducible defences. Pathogens must specialize to circumvent the defence mechanisms of the host, especially those biotrophic pathogens that derive their nutrition from an intimate association with living plant cells. If the pathogen can cause disease, the interaction is said to be compatible, but if the plant is resistant, the interaction is said to be incompatible. Race specific resistance is strongly correlated with the hypersensitive response (HR), an induced response by which (it is hypothesized) the plant deprives the pathogen of living host cells by localized cell death at sites of attempted pathogen ingress.

It has long been known that HR-associated disease resistance is often (though not exclusively) specified by dominant genes (R genes). Flor showed that when pathogens mutate to overcome such R genes, these mutations are recessive. Flor concluded that for R genes to function, there must also be corresponding genes in the pathogen, denoted avirulence genes (Avr genes). To become virulent, pathogens must thus stop making a product that activates R gene-dependent defence mechanisms (Flor, 1971). A broadly accepted working hypothesis, often termed the elicitor/receptor model, is that R genes encode products that enable plants to detect the presence of pathogens, provided said pathogens carry the corresponding Avr gene (Gabriel and Rolfe, 1990). This recognition is then transduced into the activation of a defence response.

Some interactions exhibit different genetic properties. *Helminthosporium carbonum* races that express a toxin (Hc toxin) infect maize lines that lack the Hm1 resistance gene. Mutations to loss of Hc toxin expression are recessive, and correlated with loss of virulence, in contrast to gene-for-gene interactions in which mutations to virulence are recessive. A major accomplishment was reported in 1992, with the isolation by tagging of the Hm1 gene (Johal and Briggs, 1992). Plausible arguments have been made for how gene-for-gene interactions could evolve from toxin-dependent virulence. For example, plant genes whose products were the target of the toxin might mutate to confer even greater sensitivity to the toxin, leading to HR, and the conversion of a sensitivity gene to a resistance gene. However, this does not seem to be the mode of action of Hm1, whose gene product inactivates Hc toxin.

Pathogen avirulence genes are still poorly understood. Several bacterial Avr genes encode hydrophilic proteins with no homology to other classes of protein, while others carry repeating units whose number can be modified to change the range of plants on which they exhibit avirulence (Keen, 1992; Long and Staskawicz, 1993). Additional bacterial genes (hrp genes) are required for bacterial Avr genes to induce HR, and also for pathogenicity (Keen, 1992; Long and Staskawicz, 1993). It is not clear why pathogens make products that enable the plant to detect them. It is widely believed that certain easily discarded Avr genes contribute to but are not required for pathogenicity, whereas other Avr genes are less dispensable (Keen, 1992; Long and Staskawicz, 1993). The characterization of one fungal avirulence gene has also been reported; the Avr9 gene of *Cladosporium fulvum*, which confers avirulence on *C. fulvum* races that attempt to attack tomato varieties that carry the Cf-9 gene, encodes a secreted cysteine-rich peptide with a final processed size of 28 amino acids but its role in compatible interactions is not clear (De Wit, 1992).

The technology for gene isolation based primarily on genetic criteria has improved dramatically in recent years, and many workers are currently attempting to clone a variety of R genes. Targets include (amongst others) rust resistance genes in maize, Antirrhinum and flax (by transposon tagging); downy mildew resistance genes in lettuce and Arabidopsis (by map based cloning and T-DNA tagging); *Cladosporium fulvum* (Cf) resistance genes in tomato (by tagging, map based cloning and affinity labelling with avirulence gene products); virus resistance genes in tomato and tobacco (by map based cloning and tagging); nematode resistance genes in tomato (by map based cloning); and genes for resistance to bacterial pathogens in Arabidopsis and tomato (by map based cloning).

The map based cloning of the tomato Pto gene that confers "gene-for-gene" resistance to the bacterial speck pathogen *Pseudomonas syringae* pv tomato (Pst) has been reported (Martin et al, 1993). A YAC (yeast artificial chromosome) clone was identified that carried restriction fragment length polymorphism (RFLP) markers that were very tightly linked to the gene. This YAC was used to isolate homologous cDNA clones. Two of these cDNAs were fused to a strong promoter, and after transformation of a disease sensitive tomato variety, one of these gene fusions was shown to confer resistance to Pst strains that carry the corresponding avirulence gene, AvrPto. These two cDNAs show homology to each other. Indeed, the Pto cDNA probe reveals a small gene family of at least six members, 5 of which can be found on the YAC from which Pto was isolated, and which thus comprise exactly the kind of local multigene family inferred from genetic analysis of other R gene loci. The Pto gene cDNA sequence is puzzling for proponents of the simple elicitor/receptor model. It reveals unambiguous homology to serine/threonine kinases, consistent with a role in signal transduction Intriguingly, there is strong homology to the kinases associated with self incompatibility in Brassicas, which carry out an analogous role, in that they are required to prevent the growth of genotypically defined incompatible pollen tubes. However, in contrast to the Brassica SRK kinase (Stein et al 1991), the Pto gene appears to code for little more than the kinase catalytic domain and a potential N-terminal myristoylation site that could promote association with membranes. It would be surprising if such a gene product could act alone to accomplish the specific recognition required to initiate the defence response only when the AvrPto gene is detected in invading microrganisms. The race-specific elicitor molecule made by Pst strains that carry AvrPto is still unknown and needs to be characterized before possible recognition of this molecule by the Pto gene product can be investigated.

We have now isolated the tomato Cf-9 gene which confers resistance against the fungus *Cladosporium fulvum* and we have sequenced the DNA and deduced the amino acid sequence from this gene. The DNA sequence of the tomato Cf-9 genomic gene is shown in SEQ ID NO.1 (and FIG. 2) and the deduced amino acid sequence is shown in SEQ ID NO. 2 (and FIG. 3). A cDNA sequence is shown in SEQ ID NO. 4 (and FIG. 4).

As described in more detail below, the tomato Cf-9 gene was isolated by a method which involved use of a transformed line of tomato engineered for expression of the Avr9 avirulence gene. This transformed line, which constitutively expressed functional, mature Avr9 protein, was crossed to plants which carried the Cf-9 gene so that a proportion of the progeny exhibited a necrotic phenotype culminating in seedling death. The Cf-9 gene was identified by the technique of transposon tagging with tagging of the Cf-9 gene being confirmed by survival of the resulting seedlings.

According to one aspect, the present invention provides a DNA isolate encoding a pathogen resistance gene or a fragment thereof, the gene being characterized in that it encodes the amino acid sequence shown in SEQ ID NO 2 or an amino acid sequence showing a significant degree of homology thereto.

For example, the DNA isolate comprises DNA encoding an amino acid sequence showing 60% homology, preferably 80% homology, more preferably 90% homology to the amino acid sequence shown in SEQ ID NO 2. Most preferably the DNA encodes the amino acid sequence shown in SEQ ID NO 2 in which case the DNA isolate may comprise DNA having the sequence shown in SEQ ID NO 1 or SEQ ID NO 4, or part of either of these sufficient to encode the desired polypeptide (eg from the initiating methionine codon to the first in frame downstream stop codon). In one embodiment the DNA comprises a sequence of nucleotides which are the nucleotides 1871 to 2969 of SEQ ID NO 1, or a mutant, derivative or allele thereof. A further aspect of the invention provides a DNA isolate encoding a pathogen resistance gene, or a fragment thereof, obtainable by screening a DNA library with a probe comprising nucleotides 1871 to 2969 of SEQ ID NO 1, or a fragment, derivative, mutant or allele thereof, and isolating DNA which encodes a polypeptide able to confer pathogen resistance to a plant, such as resistance to *Cladosporium fulvum* (eg. expressing Avr9). The plant may be tomato. Suitable techniques are well known in the art.

DNA according to the present invention may encode the amino acid sequence shown in SEQ ID NO 2 or a mutant, derivative or allele of the sequence provided. Preferred mutants, derivatives and alleles are those which retain a functional characteristic of the protein encoded by the wild-type gene, especially the ability to confer pathogen resistance. Changes to a sequence, to produce a mutant or derivative, may be by one or more of insertion, deletion or substitution of one or more nucleotides in the nucleic acid, leading to the insertion, deletion or subsitution of one or more amino acids. Of course, changes to the nucleic acid which make no difference to the encoded amino acid sequence are included.

The DNA isolate, which may contain the DNA encoding the amino acid sequence of SEQ ID NO 2 or an amino acid sequence showing a significant degree of homology thereto as genomic DNA or cDNA, may be in the form of a recombinant vector, for example a phage or cosmid vector. The DNA may be under the control of an appropriate promoter and regulatory elements for expression in a host cell, for example a plant cell. In the case of genomic DNA, this may contain its own promoter and regulatory elements and in the case of cDNA this may be under the control of an appropriate promoter and regulatory elements for expression in the host cell.

Those skilled in the art are well able to construct vectors and design protocols for recombinant gene expression. Suitable vectors can be chosen or constructed, containing appropriate regulatory sequences, including promoter sequences, terminator fragments, polyadenylation seuqences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press.

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material may or may not occur according to different embodiments of the invention. Finally, as far as plants are concerned the target cell type must be such that cells can be regenerated into whole plants.

Plants transformed with the DNA segment containing pre-sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (U.S. Pat. No. 5,100,792, EP-A-444882, EP-A-434616) microinjection (WO 92/09696, WO 94/00583, EP 331083, EP 175966), electroporation (EP 290395, WO 8706614) or other forms of direct DNA uptake (DE 4005152, WO 9012096, U.S. Pat. No. 4,684,611). Agrobacterium transformation is widely used by those skilled in the art to transform dicotyledonous species. Although Agrobacterium has been reported to be able to transform foreign DNA into some monocotyledonous species (WO 92/14828), microprojectile bombardment, electroporation and direct DNA uptake are preferred where Agrobacterium is inefficient or ineffective. Alternatively, a combination of different techniques may be employed to enhance the efficiency of the transformation process, eg. bombardment with Agrobacterium coated microparticles (EP-A-486234) or mircoprojectile bombardment to induce wounding followed by co-cultivation with Agrobacterium (EP-A-486233).

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention.

The Cf-9 gene and modified versions thereof encoding a protein showing a significant degree of homology to the protein product of the Cf-9 gene, alleles, mutants and derivatives thereof, may be used to confer resistance in plants, in particular tomatoes, to a pathogen such as *C. fulvum*. For this purpose a vector as described above may be used for the production of a transgenic plant. Such a plant may possess pathogen resistance conferred by the Cf-9 gene.

The invention thus further encompasses a host cell transformed with such a vector, especially a plant or a microbial cell. Thus, a host cell, such as a plant cell, comprising nucleic acid according to the present invention is provided. Within the cell, the nucleic acid may be incorporated within the chromosome.

A vector comprising nucleic acid according to the present invention need not include a promoter, particularly if the vector is to be used to introduce the nucleic acid into cells for recombination into the genome.

Also according to the invention there is provided a plant cell having incorporated into its genome a sequence of nucleotides as provided by the present invention, under operative control of a promoter for control of expression of the encoded polypeptide. A further aspect of the present invention provides a method of making such a plant cell involving introduction of a vector comprising the sequence of nucleotides into a plant cell. Such introduction may be followed by recombination between the vector and the plant cell genome to introduce the sequence of nucleotides into the genome. The polypeptide encoded by the introduced nucleic acid may then be expressed.

Plants which comprise a plant cell according to the invention are also provided, along with any part or clone thereof, seed, selfed or hybrid progeny and descendants.

The invention further provides a method of comprising expression from nucleic acid encoding the amino acid sequence SEQ ID NO 2, or a mutant, allele or derivative thereof, or a significantly homologous amino acid sequence, within cells of a plant (thereby producing the encoded polypeptide), following an earlier step of introduction of the nucleic acid into a cell of the plant or an ancestor thereof. Such a method may confer pathogen resistance on the plant.

A gene stably incorporated into the genome of a plant is passed from generation to generation to descendants of the plant, cells of which decendants may express the encoded polypeptide and so may have enhanced pathogen resistance. Pathogen resistance may be determined by assessing compatibility of a pathogen (eg. *Cladosporium fulvum*) or using recombinant expression of a pathogen avirulence gene, such as Avr9. Such a gene may be introduced into cells of a plant by any suitable transformation technique or by crossbreeding, as discussed herein.

Sequencing of the Cf-9 gene has shown that it includes DNA sequence encoding leucine-rich repeat (LRR) regions and homology searching has revealed strong homologies to other genes containing LRRs. For the reasons discussed in more detail below, the presence of LRRs can be hypothesised to be characteristic of many pathogen resistance genes and the presence of LRRs can thus be used in a method of identifying further pathogen resistance genes.

According to a further aspect, the present invention provides a method of identifying a plant pathogen resistance gene which comprises:

(1) obtaining expressed or genomic DNA from cells of a plant possessing resistance to a pathogen;

(2) sequencing the DNA and identifying putative pathogen resistance genes by the presence of LRRs; and (3) confirming identification as a pathogen resistance gene.

DNA which may contain a pathogen resistance gene can be obtained in many ways. In the course of map-based cloning of disease resistance genes, genetic analysis may identify YAC clones that may possibly carry the resistance gene. Such YAC clones could then be used to screen cDNA clones from a cDNA library, and homologous cDNA clones that mapped from the region sequenced. These sequences can then be inspected for the presence of LRRs and putative pathogen resistance genes identified on the basis of such LRRs.

Alternatively, random DNA sequences from an appropriate plant source can be obtained, for example as cDNA or as genomic DNA in a cosmid vector or YAC, and this random DNA can be sequenced and putative pathogen resistance genes identified on the basis of LRRs. A large amount of DNA sequence information has already been generated from DNA derived from many different sources and this sequence information is available in databases. Such known DNA sequences can be searched for LRRs and sequence from an appropriate source showing LRRs can again be identified as a putative pathogen resistance gene.

LRRs are already known in many different genes (see for example Chang et al 1992) so that sequences of this type can readily be identified. Identification of LRRs can be by simple visual inspection of the sequence to find areas of sequence that carry repeated motifs that are rich in leucine residues. Alternatively an appropriate computer searching technique can be used to determine homology to a known sequence containing LRRs or to a consensus sequence derived from known sequences containing LRRs. More particularly, use can be made of one or other of the various available algorithms for local sequence similarity searching such as BLASTX. Thus, for example, a BLASTX search can be used in databases at the US National Center for Biological Information and an LRR containing sequence can be identified by a BLASTX score of at least 60 or more against the sequence for Cf-9 as set out in SEQ ID NO 2.

Once a putative pathogen resistance gene has been identified, this can be investigated further, if necessary following isolation of the full coding sequence, by linkage analysis to determine the chromosome on which the gene is located and whether it is linked to known locations for pathogen resistance genes. Such linkage analysis may also give indications as to the nature of the pathogen involved. Following linkage analysis, identification of a pathogen resistance gene can be confirmed by reintroduction of the DNA back into a plant with an appropriate genotype and investigation of the effect of that DNA on the transformed plant. If the effect is to confer resistance to a specific pathogen to an otherwise non-resistant plant, then this confirms the gene as a pathogen resistance gene.

The techniques described above are of general applicability to the identification of pathogen resistance genes in plants. Examples of the type of genes that can be identified in this way include Phytophthora resistance in potatoes, mildew resistance and rust resistance in cereals such as barley and maize, rust resistance in Antirrhinum and flax, downy mildew resistance in lettuce and Arabidopsis, virus resistance in potato, tomato and tobacco, nematode resistance in tomato, resistance to bacterial pathogens in Arabidopsis and tomato and Xanthomonas resistance in peppers.

Once a pathogen resistance gene has been identified, it can be reintroduced into the plant in question by techniques well known to those skilled in the art to produce transgenic plants that have been engineered to carry the resistance gene in question. According to a further aspect, the present invention provides a DNA isolate encoding the protein product of a plant pathogen resistance gene which has been identified by use of the presence therein of LRRs and, in particular, by the technique defined above. According to a yet further aspect, the invention provides transgenic plants, in particular crop plants, which have been engineered to carry pathogen resistance genes which have been identified by the presence of LRRs. Examples of suitable plants include tobacco, cucurbits, carrot, vegetable brassica, lettuce, strawberry, oilseed brassica, sugar beet, wheat, barley, maize, rice, soyabeans, peas, sorghum, sunflower, tomato, potato, pepper, chrysanthemum, carnation, poplar, eucalyptus and pine.

Further aspects and embodiments of the patent invention will be apparent to those skilled in the art. All documents mentioned herein are incorporated by reference.

As already indicated, the present invention is based on the cloning and sequencing of the tomato Cf-9 gene and this experimental work is described in more detail below with reference to the following figures.

BRIEF DESCRIPTION OF THE DRAWINGS

FIG. 2 shows the genomic DNA sequence of the Cf-9 gene (SEQ ID NO 1). Features: Nucleic acid sequence—Translation start at nucleotide 898; translation stop at nucleotide 3487; polyadenylation signal (AATAAA) at nucleotide 3703–3708; polyadenylation site at nucleotide 3823; a 115 bp intron in the 3' non-coding sequence from nucleotide 3507/9 to nucleotide 3622/4. Predicted Protein Sequence—primary translation product 863 amino acids; signal peptide sequence amino acids 1–23; mature peptide amino acids 24–863.

FIG. 3 shows Cf-9 protein amino acid sequence (SEQ ID NO 2).

FIG. 4 shows the sequence of one of the CF9 cDNA clones (SEQ ID NO 4). Translation initiates at the ATG at position +58.

FIG. 5 shows a physical map of the tomato Cf-9 locus generated from overlapping cosmids (34, 41, 110 and 138) isolated from the Cf-2/Cf-9 cosmid library. The extent of each cosmid and location of the Cf-9 gene are shown schematically. Also indicated are the direction of the transcription (arrow) and the location of sites for restriction enzyme BglII (B).

CLONING OF THE TOMATO Cf-9 GENE

Figure 1:
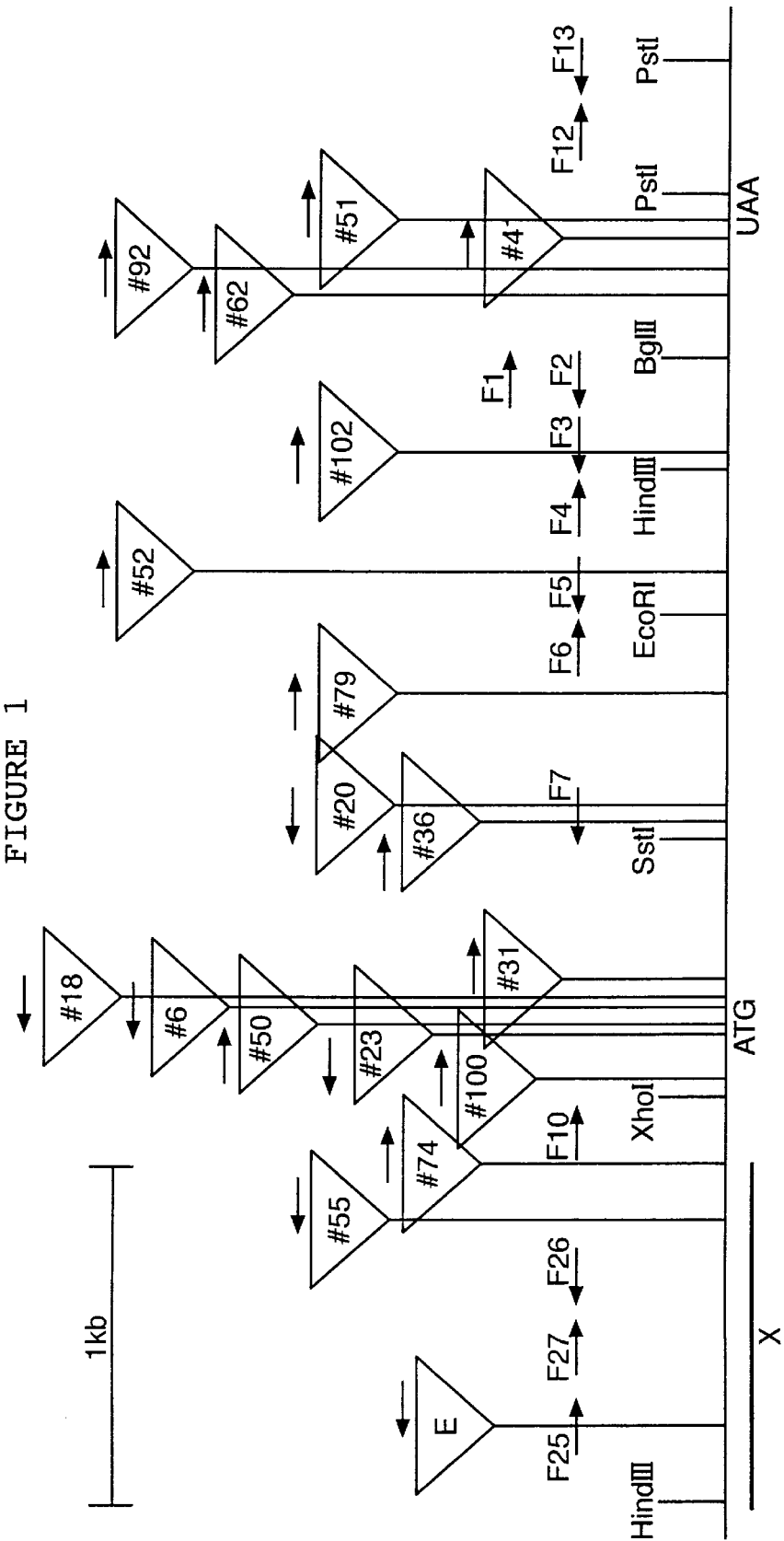
FIG. 1 shows a schematic representation of the Cf-9 gene.

As already indicated, the *C. fulvum* AVR9 gene and product are known (De Wit, 1992; van Kan et al 1991; Marmeisse et al 1993; Van Den Ackerveken et al 1993), Accordingly isolation of the Cf-9 gene would be scientifically attractive, because it should enable characterization of binding between the AVR9 gene product ligand and the presumed Cf-9 gene product receptor.

(i) Assignment of Cf- gene map locations.

We have mapped several Cf genes, including Cf-9, to their chromosomal locations (Dickinson et al 1993; Jones et al 1993; Balint-Kurti et al 1993). We showed that Cf-4 and Cf-9 map to approximately the same location on the short arm of chromosome 1, and Cf-2 and Cf-5 map to approximately the same location on chromosome 6. Others independently mapped Cf-9 to chromosome 1 (van der Beek et al 1992).

(ii) Establishing transposon tagging in tomato

We have been establishing the capacity to carry out transposon tagging in tomato using the maize transposon Activator (Ac) and its Dissociation (Ds) derivatives (Scofield et al 1992; Thomas et al 1994; Carroll et al 1995). The strategy is founded on the fact that these transposons preferentially transpose to linked sites. Accordingly we have made available lines that carry Dss at positions that are useful to our colleagues. J Hille made available a line, FT33 (Rommens et al 1992), carrying a Ds linked to Cf-9. We have independently generated our own lines that carry a construct SLJ10512 (Scofield et al 1992) which contains (a) a beta-glucuronidase (GUS) gene (Jefferson et al 1987) to monitor T-DNA segregation and (b) stable Ac (sAc) that expresses transposase and can trans-activate a Ds, but which will not transpose (Scofield et al 1992).

(iii) Establishing a stock from which gametes carrying a mutagenized Cf-9 gene could be obtained and identified The line FT33 did not carry a Cf-9 gene. We had to obtain recombinants that placed Cf-9 in cis with the T-DNA in FT33 in order to carry out linked targeted tagging. Two strategies were pursued simultaneously.

(a) FT33 was crossed to Cf9, a stock that carries the Cf-9 gene. The resulting F1 was then back crossed to Cf0 (a stock that carries no Cf- genes). Progeny that carry the FT33 T-DNA are kanamycin resistant. Kanamycin resistant progeny were tested for the presence of Cf-9; 5 *C. fulvum* resistant individuals were obtained among 180. We also generated progeny that were homozygous for Cf-9 and carried the sAc T-DNA of SLJ10512. These were crossed to the recombinants in which Cf-9 and FT33 were in cis. In the FT33 T-DNA, a transposable Ds element is cloned into a hygromycin resistance gene, preventing its function. The somatic transactivation of this Ds element, which only occurs in the presence of transposase gene expression, results in activation of the hygromycin resistance. Thus from crossing the recombinants between Cf-9 and FT33, to the sAc-carrying Cf-9 homozygotes, hygromycin resistant individuals could be obtained which carry sAc and FT33, and are likely to be homozygous for Cf-9. 140 individuals of this genotype were thus obtained.

(b) To accelerate obtaining individuals that carried sAc, FT33, and were Cf-9 homozygotes, the FT33/Cf-9 F1 was crossed to a line that was heterozygous for Cf-9 and sAc. 25% of the resulting progeny carried both T-DNAs and were hygromycin resistant, and of those, slightly more than 50% were disease resistant because they carried at least one copy of the Cf-9 gene. A restriction fragment length polymorphism (RFLP) marker was available, designated CP46, that enabled us to distinguish between homozygotes and heterozygotes for the Cf-9 gene (Balint-Kurti et al 1994 (in press)). In this manner two individuals that were Cf-9 homozygotes, and that carried both the FT33 T-DNA and sAc, were obtained. These two individuals were multiplied by taking cuttings so that more crosses could be made onto this genotype.

(iv) Establishing a tomato stock that expresses functional mature AVR9 protein

A likely frequency for obtaining any desired mutation in a gene tagging experiment is less than 1 in 1000, and often less than 1 in 10,000 (Döring, 1989). To avoid screening many thousands of plants for mutations to disease sensitivity, we established a selection for such mutations based on expressing the fungal Avr9 gene in plants. The sequence of the 28 amino acids of the mature Avr9 protein is known (van Kan et al 1991). It is a secreted protein and can be extracted from intercellular fluid of leaves infected with Avr9-carrying races of *C. fulvum*. For secretion from plant cells, we designed oligonucleotides to assemble a gene that carried a 30 amino acid plant signal peptide, from the Pr1a gene (Cornelissen et al 1987) preceding the first amino acid of the mature Avr9 protein (see SEQ ID No. 3). The preferred Avr9 gene sequence depicted in SEQ ID No. 3 is a chimaeric gene engineered from the Pr-1a signal peptide sequence (Cornelissen et al 1987) and the Avr9 gene sequence (van Kan et al, 1991). This reading frame was fused to the 35S promoter of cauliflower mosaic virus (Odell et al 1984), and the 3' terminator sequences of the octopine synthase gene (DeGreve et al 1983), and introduced into binary plasmid vectors for plant transformation, using techniques well known to those skilled in the art, and readily available plasmids (Jones et al 1992). We obtained transformed Cf0 tomato lines that expressed this gene. These transformed lines were crossed to plants that carried the Cf-9 gene. When the resulting progeny were germinated, 50% exhibited a necrotic phenotype, that culminated in seedling death. This outcome was only observed in seedlings that contained the Avr9 gene. When the same transformants were crossed to Cf0 plants, the resulting prgeny were all fully viable. From selfing the primary transformants, individuals were identified that were homozygous for the Avr9 trans-gene. When Avr9 homozygotes were crossed to Cf-9, all progeny died. This system thus provides a powerful selection for individuals that carry mutations in the Cf-9 gene (Hammond-Kosack et al 1994).

(v) Tagging the Cf-9 gene

Individuals that were homozygous for the Avr9 gene (section (iv)) were used as male parents to pollinate individuals that were homozogyous for Cf-9, and carried both sAc and the DS in the FT33 T-DNA (section (iiia) and (iiib)). Many thousands of progeny resulting from such a cross were germinated. Most died, but some survived.

DNA was obtained from survivors and subjected to Southern blot analysis using a Ds probe. It was observed that several independent mutations were correlated with insertions of the Ds into a BglII fragment of a consistent size. The same result was observed with XbaI. This sugested that several independent mutations were a consequence of insertion of the Ds into the same DNA fragment.

Using primers to the Ds sequence, DNA adjacent to the Ds in transposed Ds-carrying mutant #18 was amplified using inverse PCR (Triglia et al 1988). This DNA was be used as a probe to other mutants, and proved that in independent mutations, the Ds had inserted into the same 6.7 kb BglII fragment.

The Ds in FT33 contains a bacterial replicon and a chloramphenicol resistance gene as a bacterial selectable marker (Rommens et al 1992). This means that plant DNA carrying this transposed Ds can be digested with a restriction enzyme that does not cut within the Ds (such as BglII), the digestion products can be recircularized, and then used to transform *E. coli*. Chloramphenicol resistant clones can be obtained that carry the Ds and adjacent plant DNA. This procedure was used to obtain a clone that carried 1.7 kb of plant DNA on the 3' side of the Ds, and 4.9 kb of plant DNA on the 5' side of the Ds.

Our current understanding of the Cf-9 gene is depicted schematically in FIG. 1. The 1.8 kb of plant DNA on the 3' side of Ds extend between insertion #18 and the Bglll site on this figure. Further clones were obtained by digesting plant DNA of mutant #18 with Xbal instead of Bglll prior to recircularization and transformation. This permitted the isolation of clones carrying DNA that extended considerably (at least 5 kb) to the right of this Bglll site, and thus permitted sequencing of DNA to the right of the Bglll site shown in FIG. 1.

Using a combination of various subclones, synthesis of new sequencing primers for further sequence determination based on newly established sequence (primers F1, 2, 3, 4, 5, 6, 7, 12, 13, 10, 26, 27 and 25 that were used in such experiments are indicated in the Figure), and other techniques well known to those skilled in the art, 3847 bp of sequence were determined. Various other restriction sites (Xhol, Sstl, EcoRI and Hindlll) are also indicated in FIG. 1.

The F-series of primers were used to characterise a large number of independent mutations by PCR analysis in combination with primers based on the sequence of Ds. Therefore, these primers were used in polymerase chain reactions with primers based on the maize Ac/Ds transposon sequence, to characterise the locations of other mutations of Cf-9 that were caused by transposon insertion.

Eighteen independent insertions were characterized and are located as shown. Mutants E, #55, #74 and #100 gave incomplete survival and showed a necrotic phenotype, and based on the available sequence information, they are 5' to the actual reading frame and might permit enough cf9 protein expression to activate an incomplete defence response.

(vi) DNA sequence analysis of the Cf-9 gene

DNA sequence analysis of the Cf-9 gene has now been completed and upon conceptual translation has revealed an interesting motif (the leucine rich repeat, or LRR) that can be hypothesized to be diagnostic of other resistance genes. The genomic DNA sequence of Cf-9 is shown in FIG. 2 and SEQ ID NO. 1. Approximately 3.9 kbp of genomic DNA sequence has been determined. A translation start codon (ATG) sequence is located at position 898 and a translation termination codon TAG sequence is located at position 3487 bp (FIG. 2), with an intervening uninterrupted 863 amino acid open reading frame.

Using the sequence obtained, oligonucleotide primers were designed that could be used in PCR reactions in combination with primers based on the sequence of the Ds element, to characterize both the location and the orientation of other transposon insertions in the gene. Based on the results of such experiments, the map positions of 17 other Ds insertions can now be reliably assigned (as shown in FIG. 1).

The fact that 18 independent mutants that survive in the presence of Avr9, are associated with insertions into the same region of DNA, provides compelling evidence that the Cf-9 gene has been tagged, and that DNA sequence obtained from this region is derived from the Cf-9 gene.

Further proof is provided by the fact that when mutant # 18, (a stable mutant that lacks sAc) is back-crossed to a line homozygous for sAc, one quarter of the resulting progeny carry sAc, Ds # 18, and the Avr9 gene. These progeny exhibit variegation for a necrosis, consistent with the idea that on sAc dependent somatic excision of Ds, Cf-9 gene function is somatically restored, leading to sectors that die. Further proof is provided by the fact that individuals that survived the Avr9 selection lost disease resistance to races of *C. fulvum* that carry the Avr9 gene (Jones et al. 1994).

(vii) Identification of a leucine-rich repeat region in Cf-9.

The genomic DNA sequence of the Cf-9 gene is shown in FIG. 2 (SEQ ID NO. 1). The deduced amino acid sequence of the Cf-9 protein is shown in FIG. 3 (SEQ ID NO. 2). Currently the 18 independent Ds insertions are all in or 5' to the 863 amino acid open reading frame shown in FIG. 3. A cDNA library was constructed from messenger RNA isolated from tomato cotyledons injected with intercellular fluid containing AVR9 peptide in a bacteriophage lambda cloning vector. 600,000 cDNA clones were screened and 18 clones were identified that hybridized to DNA probes from sequences adjacent to the Ds insertions in the Cf-9 gene. While some of these cDNA clones were from other members of the Cf-9 multigene family (Jones et al 1994), six clones were identified that are derived from the genomic sequence shown in FIG. 2 because they show identical DNA sequence apart from the splicing out of a small intron in the 3' untranslated region between nucleotides 3509 and 3623 of the FIG. 2 sequence. The sequence of one such cDNA clone is shown below in FIG. 4 (SEQ ID NO. 4).

Homology searching of the resulting sequence against sequences in the databases at the US National Centre of Biological Information (NCBI) reveals strong homologies to other genes that contain leucine rich repeat regions (LRRs). These include the Arabidopsis genes TMK1 (Chang at al 1992), TMKL1 (Valon et al 1993), RLK5 (Walker, 1993), as well as expressed sequences with incomplete sequence and unknown function (e.g. *Arabidopsis thaliana* transcribed sequence [ATTS] 1447). The presence of LRRs has been observed in other genes, many of which probably function as receptors (see Chang et al (1992) for further references).

The TMK1 and RLK5 genes have structures which suggest they encode transmembrane serine/threonine kinases and carry extensive LRR regions. As yet no known function has been assigned to them. Disease resistance genes are known to encode gene products which recognize pathogen products and subsequently initiate a signal transduction chain leading to a defence response. It is known that another characterized disease resistance gene (Pto) is a protein kinase (Martin et al 1993). However, in Cf-9 there is no apparent protein kinase domain based on genomic DNA and cDNA sequence analysis.

The predicted Cf-9 amino acid sequence can be divided into 7 domains (see also FIG. 3 in Jones et al 1994):

Domain A is a 23 amino acid probable signal peptide.

Domain B is a 68 amino acid region with some homology to polygalacturonase inhibitor proteins.

Domain C is a 668 amino acid comprising 28 imperfect copies of a 24 amino acid leucine rich repeat (LRR).

Domain D is a 28 amino acid domain with some homology to polygalacturonase inhibitor proteins.

Domain E is a 18 amino acid domain rich in negatively charged residues.

Domain F is a 37 amino acid hydrophobic domain encoding a putative transmembrane domain.

Domain G is a 21 amino acid domain rich in positively charged residues.

Domains E, F and G together comprise a likely membrane anchor.

(viii) Isolation of binary cosmid vector clones that carry a genomic Cf-9 gene

In order to demonstrate that the gene characterized by transposon tagging is indeedCf-9, we have demonstrated that homologous DNA sequences from the Moneymaker Cf9 near isogenic line (the Cf9 stock) could confer both resistance to C. fulvum and sensitivity to Avr9 peptide in transgenic Cf0 tomato plants into which these sequences have been transformed.

A genomic DNA library was constructed from a stock that carried both the Cf-9 gene on chromosome 1, and the Cf-2 gene on chromosome 6, so that the library could be used for isolating both genes. The library was constructed in a binary cosmid cloning vector pCLD04541, obtained from Dr C. Dean, John Innes Centre, Colney Lane, Norwich (see also Bent et al., 1994). This vector is essentially similar to pOCA18 (Olszewski et al., 1988).

It contains a bacteriophage lambda cos site to render the vector packageable by lambda packaging extracts and is thus a cosmid (Hohn and Collins, 1980). It is also a binary vector (van den Elzen et al., 1985), so any cosmid clones that are isolated can be introduced directly into plants to test for the function of the cloned gene.

High molecular weight DNA was isolated from leaves of 6 week old greenhouse-grown plants by techniques well known to those skilled in that art (Thomas et al 1994) and partially digested with MboI restriction enzyme. The partial digestion products were size fractionated using a sucrose gradient and DNA in the size range 20–25 kilobases (kb) was ligated to BamHI digested pCLD04541 DNA, using techniques well known to those skilled in the art. After in vitro packaging using Stratagene packaging extracts, the cosmids were introduced into a tetracycline sensitive version (obtained from Stratagene) of the Stratagene *Escherichia coli* strain SURE™. Recombinants were selected using the tetracycline resistance gene on pCLD04541.

The library was randomly distributed into 144 pools containing about 1500 clones per pool, cells were grown from each pool and from 10 ml of cells, 9 ml were used for bulk plasmid DNA extractions, and 1 ml was used after addition of 0.2 ml of glycerol, to prepare a frozen 10 stock. Plasmid DNA was isolated by alkaline lysis (Birnboim and Doly, 1979), and was analyzed by PCR for pools that might carry Cf-9 homologous DNA, using the PCR primers F7 and F10 with the sequences 5'GGAAGAGATGTTTACAGAT-TCAAGG3' (SEQ ID NO 5) and 5'ATCAGCAGGTCGAT-TCTTGTGG3' (SEQ ID NO 6) respectively, that prime towards each other from positions 707–728 and 1494–1518 of the genomic DNA sequence. Pools 34, 41, 110 and 138 proved to be positive by this assay.

For each pool, approximately 10,000 colonies were plated out and inspected for Cf-9 homology by colony hybridization with a radioactive Cf-9 probe, and from each pool, single clones were isolated that carried such homology and gave a PCR product upon carrying out a PCR reaction with the F7, F10, combination of primers. These techniques are all well known to those skilled in the art.

These clones have been further characterized by Southern blot hybridization using a Cf-9 probe, and by restriction enzyme mapping. Our current assessment of the extent of contiguous DNA around Cf-9, as defined by these overlapping cosmids is shown in FIG. 5. These cosmids were subsequently used in plant transformation experiments, selecting for plant cells transformed to kanamycin resistance, using techniques well known to those skilled in the art. Transgenic tomato, tobacco and potato plants were produced (Fillatti et al., 1987; Hammond-Kosack et al., 1994; Horsch et al., 1985, Spychalla and Bevan, 1993) with at least one of each of cosmids 34, 41, 110 and 138.

(ix) Assessment of Cf-9 function in transgenic tomato, tobacco and potato

The function of a putative cloned Cf-9 gene can be assessed in transformed tomato by testing transformants not only for resistance to Avr9-carrying *C. fulvum*, but also for a necrotic response to intercellular fluid (IF) containing active Avr9 peptide. The function of a cloned Cf-9 gene in species that are not a host for *C. fulvum*, such as tobacco and potato, can only be assessed by evaluating the response to IF.

To assess the biological activity conferred upon tomato, potato and tobacco primary transformants carrying different Cf-9 cosmids, the interveinal panels of mature leaves were injected with IFs either containing or lacking Avr9 peptide. These IFs were prepared according to the procedure of de Wit and Spikman (1982). The IFs containing Avr9 peptide were obtained from either a compatible *C. fulvum* interaction involving race 0 and Cf0 plants or transgenic tobacco plants homozygous for the 35S:Avr9 construct (SLJ 6201) (Hammond-Kosack et al. 1994). The IFs lacking Avr9 were obtained from either a compatible *C. fulvum* interaction involving race 2,4,5,9 and Cf0 plants or from untransformed tobacco plants.

A summary of the results from experiments with the various cosmids introduced into tomato, tobacco and potato is shown in Table 1. All the tomato plants that carried a functional Cf-9 gene by the criterion of Avr9-induced necrosis, were also resistant to infection by *C. fulvum* races that express Avr9, unlike the *C. fulvum*—sensitive Cf0 Moneymaker variety into which the cosmid clone had not been transformed.

A Cf-9 - Avr9 - dependent grey necrotic response occurred within the IF injected leaf panels of most tomato (17 out of 23), potato (5 out of 5) and tobacco (10 out of 13) transformants by 24 hours post injection. These data indicate that the genomic Cf-9 gene, under the control of its own promoter, is functional and exhibits the expected specificity of action when introduced into various plant species, including tomato, potato and tobacco.

Further confirmation of the biological activity of Cf-9 in tobacco was obtained by crossing 5 different primary transformants carrying a single copy of cosmid 34 transformed lines B, H, I, L and M), to transgenic tobacco plants homozygous for the 35S:Avr9 T-DNA. Seedling lethality occurred in 50% of the $F_1$ progeny by 11 days after seed planting. A similar seedling lethal phenotype was obtained when tomato plants carrying Cf-9 were crossed to 35S:Avr9 expressing tomato plants (Hammond-Kosack et al. 1994). These data demonstrate the feasibility of strategies that exploit the recognition between Avr9 and Cf-9 for engineering disease resistance in transgenic plants other than tomato.

TABLE 1

| Plant Species | Trans'd Line | Cos'd #34 | Cos'd #41 | Cosmid #110 | Cosmid #138 |
|---|---|---|---|---|---|
| Tomato | A | + | + | + | + |
|  | B | + | + | + | + |
|  | C | − | + | + | + |
|  | D | − | − | + | + |
|  | E | − | + | − | + |
|  | F | − | + |  | + |
| Potato | A |  |  | + | + |
|  | B | + |  | + | + |
| Tobacco | A | − |  |  |  |
|  | B[1] | +[2] |  |  |  |
|  | C | − |  |  |  |
|  | D | + |  |  |  |
|  | E | + |  |  |  |
|  | F | + |  |  |  |
|  | G[1] | − |  |  |  |
|  | H[1] | + |  |  |  |
|  | I | + |  |  |  |
|  | J | + |  |  |  |
|  | K | + |  |  |  |
|  | L[1] | + |  |  |  |
|  | M[1] | + |  |  |  |

The response of transgenic tomato, potato and tobacco plants (primary transformants) carrying different Cf-9 cosmid constructs to intercellular fluid containing Avr-9 peptide obtained from transgenic tobacco plants homozygous for the 35S::Avr9 constructs (SLJ 6201). A plus (+) indicates that grey necrotic symptoms formed within the injected leaf panel by 24 hrs. A minus (−) indicates that there was no response. Copy numbers of cosmid inserts were determined by Southern blot analysis.

1 Single copy of cosmid 34, used for crossing with transgenic tobacco plants homozygous for the 35S::Avr9 T-DNA.

2 Plants also respond positively to IF containing Avr9 peptide obtained from a compatible C.fulvum interaction (race 0-Cf0) but give no response to two different intercellular fluids lacking Avr9 (race 2,4,5,9- Cf0) and untransformed tobacco.

KEY TO FIG. 1

FIG. 1 shows tagged alleles of the Cf-9 gene. X is a probable promoter.

SEQ ID NO 3.

The amino acid sequence and DNA sequence of the preferred form of the chimaeric Avr9 gene used as described herein.

REFERENCES

Balint-Kurti P, Jones D, Dixon M and Jones JDG (1994). RFLP linkage analysis of the Cf-4 and Cf-9 genes for resistance to *Cladosporium fulvum* in tomato. Theor.App.Genet. (1994 88 pp 691–700)

Bent, A. F., Kunkel, B. N., Dahlbeck, D., Brown, K. L., Schmidt, R., Giraudat, J., Leung, J., and Staskawicz, B. J. (1994). RPS2 of *Arabidopsis thaliana*: A leucine-rich repeat class of plant disease resistance genes. Science 265, 1856.

Birnboim, H. C. and Doly, J. (1979). A rapid alkaline extraction procedure for screening recombinant plasmid DNA. Nucl. Acids. Res 7, 1513–1520.

Carroll BJ, Klimyuk VI, Thomas CM, Bishop GJ and Jones JDG (1993). Germinal transpositions of the maize element Dissociation from T-DNA loci in tomato. Genetics (In Press)

Chang C, Schaller E, Patterson SE, Kwok SF, Meyerowitz EM and Bleecker AB (1992). The TMK1 gene from Arabidopsis codes for a protein with structural and biochemical characteristics of a receptor protein kinase. The Plant Cell 4:1263–1271

Cornelissen BJC, Horowitz J, van Kan JAL, Goldberg RB and Bol JF (1987). Structure of tobacco genes encoding pathogenesis-related proteins from the PR-1 group. Nucl.Acids.Res 15:6799–6811

De Wit, P. J. G. M. and Spikman,G. (1982) Evidence for the occurrence of race and cultivar-specific elicitors of necrosis in intercellular fluids of compatible interactions of *Cladosporium fulvum* and tomato Physiol. Plant Pathol 21 1–11

De Wit PJGM (1992).Molecular characterization of gene-for-gene systems in plant-fungus interactions and the application of avirulence genes in control of plant pathogens. Ann.Rev.Phytopathol. 30:391–418

DeGreve H, Dhaese P, Seurinck J, Lemmers S, Van Montague M and Schell J (1983). Nucleotide sequence and transcript map of the *Agrobacterium tumefaciens* Ti plasmid-encoded octopine synthase gene. J.Mol.Appl.Genet. 1:499–511

Dickinson M, Jones DA and Jones JDG (1993). Close linkage between the Cf-2/Cf-5 and Mi resistance loci in tomato. Mol.Plant Mic.Int. 6:341–347

Döring H-P (1989). Tagging genes with maize transposable elements. An overview. Maydica 34:73–88

Fillatti, J. J., Kiser, J., Rose, R., and Comai, L. (1987). Efficient transfer of a glyphosate tolerance gene into tomato using a binary *Agrobacterium tumefaciens* vector. Bio/technol 5, 726–730.

Flor HH (1971). Current status of the gene-for-gene concept. Ann.Rev.Phytopathol. 9:275–296

```
ATG GGA TTT GTT CTC TTT TCA CAA TTG CCT TCA TTT CTT CTT GTC
 M   G   F   V   L   F   S   Q   L   P   S   F   L   L   V

TCT ACA CTT CTC TTA TTC CTA GTA ATA TCC CAC TCT TGC CGT GCC
 S   T   L   L   L   F   L   V   I   S   H   S   C   R   A

TAC TGT AAC AGT TCT TGT ACA AGA GCT TTT GAC TGT CTT GGA CAA
 Y   C   N   S   S   C   T   R   A   F   D   C   L   G   Q

TGT GGA AGA TGC GAC TTT CAT AAG CTT CAA TGT GTA CAT TGA
 C   G   R   C   D   F   H   K   L   Q   C   V   H
```

Gabriel DW and Rolfe BG (1990). Working models of specific recognition in plant-microbe interactions. Ann.Rev.Phytopathol. 28:365–391

Hammond-Kosack, K., Harrison, K., and Jones, J. D. G. (1994). Developmentally regulated cell death on expression of the fungal avirulence gene Avr9 in tomato seedlings carrying the disease resistance gene Cf-9. Proceedings of the National Acadamy of Sciences USA 91 10445–10449

Hohn, B. and Collins, J. (1980). A small cosmid for efficient cloning of large DNA fragments. Gene 11, 291–298.

Horsch, R. B., Fry, J. E., Hoffmann, N. L., Eichholtz, D., Rogers, S. G., and Fraley, R. T. (1985). A simple and general method of transferring genes into plants. Science (Wash. ). 227, 1229–1231.

Jefferson RA, Kavanagh TA and Bevan MW (1987). GUS fusions: b-glucuronidase as a sensitive and versatile gene fusion marker in higher plants. EMBO.J. 6:3901–3907

Johal GS and Briggs SP (1992). Reductase activity encoded by the HM1 disease resistance gene in maize. Science (Wash.). 258:985–987

Jones DA, Dickinson MJ, Balint-Kurti P, Dixon M and Jones JDG (1993). Two complex resistance loci revealed in tomato by classical and RFLP mapping of the Cf-2, Cf-4, Cf-5 and Cf-9 genes for resistance to *Cladosporium Fulvum*. Mol.Plant Mic.Int. 6:348–357

Jones JDG, Shlumukov L, Carland F, English J, Scofield S, Bishop G and Harrison K (1992). Effective vectors for transformation, expression of heterologous genes, and assaying transposon excision in transgenic plants. Transgen. Res. 1:285–297

Jones, D. A., Thomas, C. M., Hammond-Kosack, K., Balint-Kurti, P. J., and Jones, J. D. G. (1994). Isolation of the tomato Cf-9 gene for resistance to *Cladosporium fulvum* by transposon tagging. Science (Wash. ).266 789–793

Keen NT (1992). Gene-for-gene complementarity in plant-pathogen interactions. Ann.Rev.Gen. 24:447–463

Long SR and Staskawicz BJ (1993). Prokaryotic Plant Parasites. Cell 73:921–935

Marmeisse R, Van Den Ackerveken GFJM, Goosen T, De Wit PJGM and Van den Broek HWJ (1993). Disruption of the avirulence gene avr9 in two races of the tomato pathogen *Cladosporium fulvum* causes virulence on tomato genotypes with the complementary resistance gene Cf9. MPMI 6:412–417

Martin GB, Brommonschenkel SH, Chunwongse J, Frary A, Ganal MW, Spivey R, Wu T, Earle ED and Tanksley SD (1993). Map-based cloning of a protein kinase gene conferring disease resistance in tomato. Science 262:1432–1436

Odell JT, Nagy F and Chua N-H (1984). Identification of DNA sequences required for activity of the cauliflower mosaic visrus 35S promoter. Nature 313:810–812

Olszewski, N. E., Martin, F. B., and Ausubel, F. M. (1988). Specialized binary vectors for plant transformation: expression of the *Arabidopsis thaliana* AHAS gene in *Nicotiana tobacum*. Nucl. Acids. Res 16, 10765–10782.

Rommens CMT, Rudenko GN, Dijkwel PP, van Haaren MJJ, Ouwerkerk PBF, Blok KM, Nijkamp HJJ and Hille J (1992). Characterization of Ac/Ds behaviour in transgenic tomato plants using plasmid rescue. Pl.Molec.Biol. 20:61–70

Scofield S, Harrison KA, Nurrish SJ and Jones JDG (1992). Promoter fusions to the Ac transposase gene confer distinct patterns of Ds somatic and germinal excision in tobacco. The Plant Cell 4:573–582

Spychalla,J. and Bevan, M. (1993) in Plant Tissue Culture Manual B11, Kluwer Academic Press Stein JC, Howlett B, Boyes DC, Nasrallah ME and Nasrallah JB (1991). Molecular cloning of a putative receptor protein kinase gene encoded at the self-incompatibility locus of *Brassica oleracea*. Proc.Natl.Acad.Sci.USA 88:8816–8820

Thomas, C. M., English, J. J., Carroll, B. J., Bennetzen, J. L., Harrison, K. A., and Jones, J. D. G. (1994). Analysis of the chromosomal distribution of transposon-carrying T-DNAs in tomato using the inverse polymerase chain reaction. Molecular and General Genetics 242, 573–585.

Triglia T. Peterson MG and Kemp DJ (1988). A procedure for in vitro amplification of DNA segments that lie outside the boundaries of known sequences. Nucleic Acids Res. 16:8186

Valon C, Smalle J, Goodman HM and Giraudat J (1993). Characterization of an *Arabidopsis thaliana* gene (TMKL1) encoding a putative transmembrane protein with an unusual kinase-like domain. Pl.Molec.Biol. 23:415–421 van den Elzen, P., Lee, K. Y., Townsend, J., and Bedbrook, J. (1985). Simple binary vectors for DNA transfer to plant cells. Plant. Mol. Biol. 5, 149–154.

van Kan JAL, Van Den Ackerveken GFJM and De Wit PJGM (1991). Cloning and characterization of cDNA of avirulence gene avr9 of the fungal pathogen *Cladosporium fulvum*, causal agent of tomato leaf mold. MPMI 4:52–59 van der Beek JG, Verkerk R, Zabel P and Lindhout P (1992). Mapping strategy for resistance genes in tomato based on RFLPs between cultivars: Cf9 (resistance to *Cladosporium fulvum*) on chromosome 1. Theor.App.Genet. 84:106–112 van Den Ackerveken GFJM, Vossen P and De Wit PJGM (1993). The AVR9 race-specific elicitor of *Cladosporium fulvum* is processed by endogenous and plant proteases. Plant Physiol. Walker JC (1993). Receptor-like protein kinase genes for *Arabidopsis thaliana*. Plant Journal 3:451–456

We claim:

1. A DNA isolate encoding a pathogen resistance gene (R gene), the pathogen resistance gene (R gene) including a nucleotide sequence encoding a polypeptide with the sequence of SEQ ID NO:2 and able to confer *Cladosporium fulvum* pathogen resistance on a tomato plant.

2. A DNA isolate as claimed in claim 1 which comprises DNA having the sequence shown in SEQ ID NO: 1 or SEQ ID NO: 4.

3. A DNA isolate in which DNA as claimed in claim 1 is under control of an appropriate promoter and regulatory elements for expression in a host cell.

4. A host cell comprising a DNA isolate according to claim 1.

5. A host cell according to claim 4 which is a microbial cell.

6. A host cell according to claim 4 which is a plant cell.

7. A plant or any part thereof comprising a plant cell according to claim 6.

8. Seed, selfed or hybrid progeny or a descendant of a plant according to claim 7, or any part thereof comprising a host plant cell comprising a DNA isolate encoding a pathogen resistance gene (R gene), the pathogen resistance gene (R gene) including a nucleotide sequence encoding a polypeptide with the sequence of SEQ ID NO:2 and able to confer *Cladosporium fulvum* pathogen resistance on a tomato plant.

9. A method of conferring *Cladosporium fulvum* pathogen resistance on a tomato plant, comprising expressing a pathogen resistance gene (R gene), the pathogen resistance gene (R gene) including a nucleotide sequence encoding a polypeptide with the sequence of SEQ ID NO: 2 and able to confer *Cladosporium fulvum* pathogen resistance on a tomato plant within cells of the plant, following an earlier step of introduction of nucleic acid comprising the pathogen resistance gene (R gene) into a cell of the plant or an ancestor thereof.

10. A method according to claim 9 wherein the nucleic acid comprises the sequence shown in SEQ ID NO:1 or SEQ ID NO:4.

11. A method of identifying a plant pathogen resistance gene (R gene) which comprises:
   (1) obtaining expressed or genomic DNA from cells of a plant possessing resistance to a pathogen;
   (2) sequenceing the DNA and identifying putative pathogen resistance genes (R genes) by the presence of leucine rich repeats (LRRs), and
   (3) confirming identification as a pathogen resistance gene (R genes).

12. A method as claimed in claim 11 wherein DNA encoding LRRs are identified as having a BLASTX score of 60 or more when compared to a sequence encoding SEQ ID NO: 2.

13. A method according to claim 11 wherein identification as a pathogen resistance gene (R gene) is confirmed by linkage analysis and/or the effect of the gene on the phenotype of an appropriate plant transformed therewith.

14. A DNA isolate in which DNA as claimed in claim 2 is under control of an appropriate promoter and regulatory elements for expression in a host cell.

15. A host cell comprising a DNA isolate according to claim 14.

16. A host cell according to claim 15 which is a plant cell.

17. A plant or any part thereof comprising a plant cell according to claim 16.

18. Seed, selfed or hybrid progeny or a descendent of a plant according to claim 17, or any part thereof, comprising a host plant cell comprising DNA having the sequence shown in SEQ ID NO:1 or SEQ ID NO:4 under the control of an appropriate promoter and regulatory elements for expression in said plant host cell.

19. A host cell comprising a DNA isolate according to claim 2.

20. A host cell according to claim 19 which is a plant cell.

21. A plant or any part thereof comprising a plant cell according to claim 20.

22. Seed, selfed or hybrid progeny or a descendent of a plant according to claim 21, or any part thereof, comprising a host plant cell comprising DNA having the sequence shown in SEQ ID NO:1 or SEQ ID NO:4.

23. A DNA molecule consisting of a pathogen resistance gene (R gene) which encodes a polypeptide with the sequence of SEQ ID NO:2.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
        (A) LENGTH: 3905 base pairs
        (B) TYPE: nucleic acid

```
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 898..3489

(ix) FEATURE:
        (A) NAME/KEY: mat_peptide
        (B) LOCATION: 967..3486

(ix) FEATURE:
        (A) NAME/KEY: sig_peptide
        (B) LOCATION: 898..966

(xi) SEQUENCE DESCRIPTION: SEQ ID NO: 1:
```

| | | |
|---|---|---|
| CATAGTCTTT GCATATTTGG ATTAAACAGG GGCATTATTG AACCAAACTA TTAGATGTAT | 60 |
| GAAAATTTTG GACCAAGCTA TTGACAACAC GAACATTTTT AGACCAAACT ATTAACTCAG | 120 |
| AATATTTTCC GTTGAATGAA TAAGGTAACT AGTAGTAAAT TTTTAGACCA AACTATGAAG | 180 |
| AACATGCCAT GTCTGGACTC CTGCACTATC TTCCATCAAC AGGTCAATTC TCTCAACTCT | 240 |
| ATTGGTGGAA GGTAGACGGT ACAAATTGAA TTATATTAAA AGACAAGCTC ACCTGAGCAT | 300 |
| CACTGTTATA CAACAACAAC AAACTACGCT TCAGCCCCAA ACAATAGTGA CCCGAATCAT | 360 |
| ATATTGTCAC GAGTTTTTTT TAGAGTATGT TGCATATATT ATACTCAACT TAGGGTTTGT | 420 |
| CATTCTGATG CTTCGTACAA ATTTATTGAA TTTTCAACTT TAAAGGTTTA TGAACCAAAT | 480 |
| ATTACGCTTA CTATGATAGC GGTCTTTTTT GATTAATCAA ACTTATTGAA TTTTCAACTT | 540 |
| TAAAGGTTTT TCCCCGTTCT ATACACAAAC TAAGAAAAAT TTAAATTATA TAGTCTTTGG | 600 |
| ATGGTGACCT ATTTGGATGG TAACATTATT GGACCAAACT ATTGATAACG CGGACATTGT | 660 |
| TAGACCAAAC TGAGAAGGAC ATGTCTGGAC TCCTGCTCCG TCTTCCATCA GCAGGTCGAT | 720 |
| TCTTGTGGAA AATTAGCTCG AGGTGGCGCA CTATGTGAGG TAACTAGTAC TAAATTTTTC | 780 |
| TTTGCTTAAT TTGTGCTATA TATACCTCAT CTAAATTATT GAATAGTCAC ACAAAGCAAA | 840 |
| CATTTCTTGA TTTCTTCTCT ATCAACATAA CAAGTTTTGA TCATTTTTAG TGCAGAA | 897 |

```
ATG GAT TGT GTA AAA CTT GTA TTC CTT ATG CTA TAT ACC TTT CTC TGT       945
Met Asp Cys Val Lys Leu Val Phe Leu Met Leu Tyr Thr Phe Leu Cys
-23         -20              -15              -10

CAA CTT GCT TTA TCC TCA TCC TTG CCT CAT TTG TGC CCC GAA GAT CAA       993
Gln Leu Ala Leu Ser Ser Ser Leu Pro His Leu Cys Pro Glu Asp Gln
        -5                  1               5

GCT CTT TCT CTT CTA CAA TTC AAG AAC ATG TTT ACC ATT AAT CCT AAT      1041
Ala Leu Ser Leu Leu Gln Phe Lys Asn Met Phe Thr Ile Asn Pro Asn
 10              15              20              25

GCT TCT GAT TAT TGT TAC GAC ATA AGA ACA TAC GTA GAC ATT CAG TCA      1089
Ala Ser Asp Tyr Cys Tyr Asp Ile Arg Thr Tyr Val Asp Ile Gln Ser
             30              35              40

TAT CCA AGA ACT CTT TCT TGG AAC AAA AGC ACA AGT TGC TGC TCA TGG      1137
Tyr Pro Arg Thr Leu Ser Trp Asn Lys Ser Thr Ser Cys Cys Ser Trp
         45              50              55

GAT GGC GTT CAT TGT GAC GAG ACG ACA GGA CAA GTG ATT GCG CTT GAC      1185
Asp Gly Val His Cys Asp Glu Thr Thr Gly Gln Val Ile Ala Leu Asp
     60              65              70

CTC CGT TGC AGC CAA CTT CAA GGC AAG TTT CAT TCC AAT AGT AGC CTC      1233
Leu Arg Cys Ser Gln Leu Gln Gly Lys Phe His Ser Asn Ser Ser Leu
 75              80              85

TTT CAA CTC TCC AAT CTC AAA AGG CTT GAT TTG TCT TTT AAT AAT TTC      1281
Phe Gln Leu Ser Asn Leu Lys Arg Leu Asp Leu Ser Phe Asn Asn Phe
 90              95              100             105
```

```
ACT GGA TCA CTC ATT TCA CCA AAA TTT GGT GAG TTT TCA AAT TTG ACG       1329
Thr Gly Ser Leu Ile Ser Pro Lys Phe Gly Glu Phe Ser Asn Leu Thr
            110                 115                 120

CAT CTC GAT TTG TCG CAT TCT AGT TTT ACA GGT CTA ATT CCT TCT GAA       1377
His Leu Asp Leu Ser His Ser Ser Phe Thr Gly Leu Ile Pro Ser Glu
            125                 130                 135

ATC TGT CAC CTT TCT AAA CTA CAC GTT CTT CGT ATA TGT GAT CAA TAT       1425
Ile Cys His Leu Ser Lys Leu His Val Leu Arg Ile Cys Asp Gln Tyr
            140                 145                 150

GGG CTT AGT CTT GTA CCT TAC AAT TTT GAA CTG CTC CTT AAG AAC TTG       1473
Gly Leu Ser Leu Val Pro Tyr Asn Phe Glu Leu Leu Leu Lys Asn Leu
        155                 160                 165

ACC CAA TTA AGA GAG CTC AAC CTT GAA TCT GTA AAC ATC TCT TCC ACT       1521
Thr Gln Leu Arg Glu Leu Asn Leu Glu Ser Val Asn Ile Ser Ser Thr
170                 175                 180                 185

ATT CCT TCA AAT TTC TCT TCT CAT TTA ACA ACT CTA CAA CTT TCA GGC       1569
Ile Pro Ser Asn Phe Ser Ser His Leu Thr Thr Leu Gln Leu Ser Gly
                190                 195                 200

ACA GAG TTA CAT GGG ATA TTG CCC GAA AGA GTT TTT CAC CTT TCC AAC       1617
Thr Glu Leu His Gly Ile Leu Pro Glu Arg Val Phe His Leu Ser Asn
            205                 210                 215

TTA CAA TCC CTT CAT TTA TCA GTC AAT CCC CAG CTC ACG GTT AGG TTT       1665
Leu Gln Ser Leu His Leu Ser Val Asn Pro Gln Leu Thr Val Arg Phe
        220                 225                 230

CCC ACA ACC AAA TGG AAT AGC AGT GCA TCA CTC ATG ACG TTA TAC GTC       1713
Pro Thr Thr Lys Trp Asn Ser Ser Ala Ser Leu Met Thr Leu Tyr Val
    235                 240                 245

GAT AGT GTG AAT ATT GCT GAT AGG ATA CCT AAA TCA TTT AGC CAT CTA       1761
Asp Ser Val Asn Ile Ala Asp Arg Ile Pro Lys Ser Phe Ser His Leu
250                 255                 260                 265

ACT TCA CTT CAT GAG TTG TAC ATG GGT CGT TGT AAT CTG TCA GGG CCT       1809
Thr Ser Leu His Glu Leu Tyr Met Gly Arg Cys Asn Leu Ser Gly Pro
                270                 275                 280

ATT CCT AAA CCT CTA TGG AAT CTC ACC AAC ATA GTG TTT TTG CAC CTT       1857
Ile Pro Lys Pro Leu Trp Asn Leu Thr Asn Ile Val Phe Leu His Leu
            285                 290                 295

GGT GAT AAC CAT CTT GAA GGA CCA ATT TCC CAT TTC ACG ATA TTT GAA       1905
Gly Asp Asn His Leu Glu Gly Pro Ile Ser His Phe Thr Ile Phe Glu
        300                 305                 310

AAG CTC AAG AGG TTA TCA CTT GTA AAT AAC AAC TTT GAT GGC GGA CTT       1953
Lys Leu Lys Arg Leu Ser Leu Val Asn Asn Asn Phe Asp Gly Gly Leu
    315                 320                 325

GAG TTC TTA TCC TTT AAC ACC CAA CTT GAA CGG CTA GAT TTA TCA TCC       2001
Glu Phe Leu Ser Phe Asn Thr Gln Leu Glu Arg Leu Asp Leu Ser Ser
330                 335                 340                 345

AAT TCC CTA ACT GGT CCA ATT CCA TCC AAC ATA AGC GGA CTT CAA AAC       2049
Asn Ser Leu Thr Gly Pro Ile Pro Ser Asn Ile Ser Gly Leu Gln Asn
                350                 355                 360

CTA GAA TGT CTC TAC TTG TCA TCA AAC CAC TTG AAT GGG AGT ATA CCT       2097
Leu Glu Cys Leu Tyr Leu Ser Ser Asn His Leu Asn Gly Ser Ile Pro
            365                 370                 375

TCC TGG ATA TTC TCC CTT CCT TCA CTG GTT GAG TTA GAC TTG AGC AAT       2145
Ser Trp Ile Phe Ser Leu Pro Ser Leu Val Glu Leu Asp Leu Ser Asn
        380                 385                 390

AAC ACT TTC AGT GGA AAA ATT CAA GAG TTC AAG TCC AAA ACA TTA AGT       2193
Asn Thr Phe Ser Gly Lys Ile Gln Glu Phe Lys Ser Lys Thr Leu Ser
    395                 400                 405

GCC GTT ACT CTA AAA CAA AAT AAG CTG AAA GGT CGT ATT CCG AAT TCA       2241
Ala Val Thr Leu Lys Gln Asn Lys Leu Lys Gly Arg Ile Pro Asn Ser
410                 415                 420                 425
```

```
CTC CTA AAC CAG AAG AAC CTA CAA TTA CTT CTC CTT TCA CAC AAT AAT        2289
Leu Leu Asn Gln Lys Asn Leu Gln Leu Leu Leu Leu Ser His Asn Asn
            430                 435                 440

ATC AGT GGA CAT ATT TCT TCA GCT ATC TGC AAT CTG AAA ACA TTG ATA        2337
Ile Ser Gly His Ile Ser Ser Ala Ile Cys Asn Leu Lys Thr Leu Ile
            445                 450                 455

TTG TTA GAC TTG GGA AGT AAT AAT TTG GAG GGA ACA ATC CCA CAA TGC        2385
Leu Leu Asp Leu Gly Ser Asn Asn Leu Glu Gly Thr Ile Pro Gln Cys
            460                 465                 470

GTG GTT GAG AGG AAC GAA TAC CTT TCG CAT TTG GAT TTG AGC AAA AAC        2433
Val Val Glu Arg Asn Glu Tyr Leu Ser His Leu Asp Leu Ser Lys Asn
        475                 480                 485

AGA CTT AGT GGG ACA ATC AAT ACA ACT TTT AGT GTT GGA AAC ATT TTA        2481
Arg Leu Ser Gly Thr Ile Asn Thr Thr Phe Ser Val Gly Asn Ile Leu
490                 495                 500                 505

AGG GTC ATT AGC TTG CAC GGG AAT AAG CTA ACG GGG AAA GTC CCA CGA        2529
Arg Val Ile Ser Leu His Gly Asn Lys Leu Thr Gly Lys Val Pro Arg
                510                 515                 520

TCT ATG ATC AAT TGC AAG TAT TTG ACA CTA CTT GAT CTA GGT AAC AAT        2577
Ser Met Ile Asn Cys Lys Tyr Leu Thr Leu Leu Asp Leu Gly Asn Asn
            525                 530                 535

ATG TTG AAT GAC ACA TTT CCA AAC TGG TTG GGA TAC CTA TTT CAA TTG        2625
Met Leu Asn Asp Thr Phe Pro Asn Trp Leu Gly Tyr Leu Phe Gln Leu
            540                 545                 550

AAG ATT TTA AGC TTG AGA TCA AAT AAG TTG CAT GGT CCC ATC AAA TCT        2673
Lys Ile Leu Ser Leu Arg Ser Asn Lys Leu His Gly Pro Ile Lys Ser
            555                 560                 565

TCA GGG AAT ACA AAC TTG TTT ATG GGT CTT CAA ATT CTT GAT CTA TCA        2721
Ser Gly Asn Thr Asn Leu Phe Met Gly Leu Gln Ile Leu Asp Leu Ser
570                 575                 580                 585

TCT AAT GGA TTT AGT GGG AAT TTA CCC GAA AGA ATT TTG GGG AAT TTG        2769
Ser Asn Gly Phe Ser Gly Asn Leu Pro Glu Arg Ile Leu Gly Asn Leu
                590                 595                 600

CAA ACC ATG AAG GAA ATT GAT GAG AGT ACA GGA TTC CCA GAG TAT ATT        2817
Gln Thr Met Lys Glu Ile Asp Glu Ser Thr Gly Phe Pro Glu Tyr Ile
            605                 610                 615

TCT GAT CCA TAT GAT ATT TAT TAC AAT TAT TTG ACG ACA ATT TCT ACA        2865
Ser Asp Pro Tyr Asp Ile Tyr Tyr Asn Tyr Leu Thr Thr Ile Ser Thr
            620                 625                 630

AAG GGA CAA GAT TAT GAT TCT GTT CGA ATT TTG GAT TCT AAC ATG ATT        2913
Lys Gly Gln Asp Tyr Asp Ser Val Arg Ile Leu Asp Ser Asn Met Ile
            635                 640                 645

ATC AAT CTC TCA AAG AAC AGA TTT GAA GGT CAT ATT CCA AGC ATT ATT        2961
Ile Asn Leu Ser Lys Asn Arg Phe Glu Gly His Ile Pro Ser Ile Ile
650                 655                 660                 665

GGA GAT CTT GTT GGA CTT CGT ACG TTG AAC TTG TCT CAC AAT GTC TTG        3009
Gly Asp Leu Val Gly Leu Arg Thr Leu Asn Leu Ser His Asn Val Leu
                670                 675                 680

GAA GGT CAT ATA CCG GCA TCA TTT CAA AAT TTA TCA GTA CTC GAA TCT        3057
Glu Gly His Ile Pro Ala Ser Phe Gln Asn Leu Ser Val Leu Glu Ser
            685                 690                 695

TTG GAT CTC TCA TCT AAT AAA ATC AGC GGA GAA ATT CCG CAG CAG CTT        3105
Leu Asp Leu Ser Ser Asn Lys Ile Ser Gly Glu Ile Pro Gln Gln Leu
            700                 705                 710

GCA TCC CTC ACA TTC CTT GAA GTC TTA AAT CTC TCT CAC AAT CAT CTT        3153
Ala Ser Leu Thr Phe Leu Glu Val Leu Asn Leu Ser His Asn His Leu
            715                 720                 725

GTT GGA TGC ATC CCC AAA GGA AAA CAA TTT GAT TCG TTC GGG AAC ACT        3201
Val Gly Cys Ile Pro Lys Gly Lys Gln Phe Asp Ser Phe Gly Asn Thr
730                 735                 740                 745
```

```
TCG TAC CAA GGG AAT GAT GGG TTA CGC GGA TTT CCA CTC TCA AAA CTT    3249
Ser Tyr Gln Gly Asn Asp Gly Leu Arg Gly Phe Pro Leu Ser Lys Leu
            750                 755                 760

TGT GGT GGT GAA GAT CAA GTG ACA ACT CCA GCT GAG CTA GAT CAA GAA    3297
Cys Gly Gly Glu Asp Gln Val Thr Thr Pro Ala Glu Leu Asp Gln Glu
            765                 770                 775

GAG GAG GAA GAA GAT TCA CCA ATG ATC AGT TGG CAG GGG GTT CTC GTG    3345
Glu Glu Glu Glu Asp Ser Pro Met Ile Ser Trp Gln Gly Val Leu Val
            780                 785                 790

GGT TAC GGT TGT GGA CTT GTT ATT GGA CTG TCC GTA ATA TAC ATA ATG    3393
Gly Tyr Gly Cys Gly Leu Val Ile Gly Leu Ser Val Ile Tyr Ile Met
            795                 800                 805

TGG TCA ACT CAA TAT CCA GCA TGG TTT TCG AGG ATG GAT TTA AAG TTG    3441
Trp Ser Thr Gln Tyr Pro Ala Trp Phe Ser Arg Met Asp Leu Lys Leu
810                 815                 820                 825

GAA CAC ATA ATT ACT ACG AAA ATG AAA AAG CAC AAG AAA AGA TAT        3496
Glu His Ile Ile Thr Thr Lys Met Lys Lys His Lys Lys Arg Tyr
                830                 835                 840

CTATACCTCC AGGTATTCCA CTTGATCATT ATCTTTCAGA AGATTATTTT TTGTATATCG  3556
TAGTGAGT

ATGAAATTAT CGACCTCCTT CATCCTCAAA GCTCTTAACT TTCACTCTTC ATTTTTGAAA  3616

ATTTCAGGAT TCAAAGATTT CCGAGTTCCC AGTTGCTTGG GATGCAGATA AAAGCCTTTT  3676

TATCTTTCAT AGTTTCTTAT CCTATGAATA AAGATTTTAT TTTCATTTGT CTATGGCACG  3736

TAGATATGTT CCGTCACTAA AAACATTGTA TTTCTCTCAA CTCTTTCGTC ACATGATATC  3796

AAAGAACACT TGACTTCAAT TAAGTTACTG TAGTCTGCTA TTTTAATTTT TTCCATTGAA  3856

ACACAACTGA CGTATCTTGA GAAAGAGACT ATGATCCCCC GGGCTGCAG              3905
```

(2) INFORMATION FOR SEQ ID NO: 2:

(i) SEQUENCE CHARACTERISTICS:
        (A) LENGTH: 863 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Asp Cys Val Lys Leu Val Phe Leu Met Leu Tyr Thr Phe Leu Cys
-23             -20                 -15                 -10

Gln Leu Ala Leu Ser Ser Ser Leu Pro His Leu Cys Pro Glu Asp Gln
        -5                  1                   5

Ala Leu Ser Leu Leu Gln Phe Lys Asn Met Phe Thr Ile Asn Pro Asn
10                  15                  20                  25

Ala Ser Asp Tyr Cys Tyr Asp Ile Arg Thr Tyr Val Asp Ile Gln Ser
                30                  35                  40

Tyr Pro Arg Thr Leu Ser Trp Asn Lys Ser Thr Ser Cys Cys Ser Trp
            45                  50                  55

Asp Gly Val His Cys Asp Glu Thr Thr Gly Gln Val Ile Ala Leu Asp
            60                  65                  70

Leu Arg Cys Ser Gln Leu Gln Gly Lys Phe His Ser Asn Ser Ser Leu
        75                  80                  85

Phe Gln Leu Ser Asn Leu Lys Arg Leu Asp Leu Ser Phe Asn Asn Phe
90                  95                  100                 105

Thr Gly Ser Leu Ile Ser Pro Lys Phe Gly Glu Phe Ser Asn Leu Thr
                110                 115                 120
```

-continued

His Leu Asp Leu Ser His Ser Ser Phe Thr Gly Leu Ile Pro Ser Glu
              125                 130                 135

Ile Cys His Leu Ser Lys Leu His Val Leu Arg Ile Cys Asp Gln Tyr
              140                 145                 150

Gly Leu Ser Leu Val Pro Tyr Asn Phe Glu Leu Leu Leu Lys Asn Leu
              155                 160                 165

Thr Gln Leu Arg Glu Leu Asn Leu Glu Ser Val Asn Ile Ser Ser Thr
170                 175                 180                 185

Ile Pro Ser Asn Phe Ser Ser His Leu Thr Thr Leu Gln Leu Ser Gly
              190                 195                 200

Thr Glu Leu His Gly Ile Leu Pro Glu Arg Val Phe His Leu Ser Asn
              205                 210                 215

Leu Gln Ser Leu His Leu Ser Val Asn Pro Gln Leu Thr Val Arg Phe
              220                 225                 230

Pro Thr Thr Lys Trp Asn Ser Ser Ala Ser Leu Met Thr Leu Tyr Val
              235                 240                 245

Asp Ser Val Asn Ile Ala Asp Arg Ile Pro Lys Ser Phe Ser His Leu
250                 255                 260                 265

Thr Ser Leu His Glu Leu Tyr Met Gly Arg Cys Asn Leu Ser Gly Pro
              270                 275                 280

Ile Pro Lys Pro Leu Trp Asn Leu Thr Asn Ile Val Phe Leu His Leu
              285                 290                 295

Gly Asp Asn His Leu Glu Gly Pro Ile Ser His Phe Thr Ile Phe Glu
              300                 305                 310

Lys Leu Lys Arg Leu Ser Leu Val Asn Asn Asn Phe Asp Gly Gly Leu
              315                 320                 325

Glu Phe Leu Ser Phe Asn Thr Gln Leu Glu Arg Leu Asp Leu Ser Ser
330                 335                 340                 345

Asn Ser Leu Thr Gly Pro Ile Pro Ser Asn Ile Ser Gly Leu Gln Asn
              350                 355                 360

Leu Glu Cys Leu Tyr Leu Ser Ser Asn His Leu Asn Gly Ser Ile Pro
              365                 370                 375

Ser Trp Ile Phe Ser Leu Pro Ser Leu Val Glu Leu Asp Leu Ser Asn
              380                 385                 390

Asn Thr Phe Ser Gly Lys Ile Gln Glu Phe Lys Ser Lys Thr Leu Ser
              395                 400                 405

Ala Val Thr Leu Lys Gln Asn Lys Leu Lys Gly Arg Ile Pro Asn Ser
410                 415                 420                 425

Leu Leu Asn Gln Lys Asn Leu Gln Leu Leu Leu Ser His Asn Asn
              430                 435                 440

Ile Ser Gly His Ile Ser Ser Ala Ile Cys Asn Leu Lys Thr Leu Ile
              445                 450                 455

Leu Leu Asp Leu Gly Ser Asn Asn Leu Glu Gly Thr Ile Pro Gln Cys
              460                 465                 470

Val Val Glu Arg Asn Glu Tyr Leu Ser His Leu Asp Leu Ser Lys Asn
              475                 480                 485

Arg Leu Ser Gly Thr Ile Asn Thr Thr Phe Ser Val Gly Asn Ile Leu
490                 495                 500                 505

Arg Val Ile Ser Leu His Gly Asn Lys Leu Thr Gly Lys Val Pro Arg
              510                 515                 520

Ser Met Ile Asn Cys Lys Tyr Leu Thr Leu Leu Asp Leu Gly Asn Asn
              525                 530                 535

Met Leu Asn Asp Thr Phe Pro Asn Trp Leu Gly Tyr Leu Phe Gln Leu
              540                 545                 550

```
Lys Ile Leu Ser Leu Arg Ser Asn Lys Leu His Gly Pro Ile Lys Ser
    555                 560                 565

Ser Gly Asn Thr Asn Leu Phe Met Gly Leu Gln Ile Leu Asp Leu Ser
570                 575                 580                 585

Ser Asn Gly Phe Ser Gly Asn Leu Pro Glu Arg Ile Leu Gly Asn Leu
            590                 595                 600

Gln Thr Met Lys Glu Ile Asp Glu Ser Thr Gly Phe Pro Glu Tyr Ile
                605                 610                 615

Ser Asp Pro Tyr Asp Ile Tyr Tyr Asn Tyr Leu Thr Thr Ile Ser Thr
            620                 625                 630

Lys Gly Gln Asp Tyr Asp Ser Val Arg Ile Leu Asp Ser Asn Met Ile
    635                 640                 645

Ile Asn Leu Ser Lys Asn Arg Phe Glu Gly His Ile Pro Ser Ile Ile
650                 655                 660                 665

Gly Asp Leu Val Gly Leu Arg Thr Leu Asn Leu Ser His Asn Val Leu
                670                 675                 680

Glu Gly His Ile Pro Ala Ser Phe Gln Asn Leu Ser Val Leu Glu Ser
            685                 690                 695

Leu Asp Leu Ser Ser Asn Lys Ile Ser Gly Glu Ile Pro Gln Gln Leu
        700                 705                 710

Ala Ser Leu Thr Phe Leu Glu Val Leu Asn Leu Ser His Asn His Leu
    715                 720                 725

Val Gly Cys Ile Pro Lys Gly Lys Gln Phe Asp Ser Phe Gly Asn Thr
730                 735                 740                 745

Ser Tyr Gln Gly Asn Asp Gly Leu Arg Gly Phe Pro Leu Ser Lys Leu
                750                 755                 760

Cys Gly Gly Glu Asp Gln Val Thr Thr Pro Ala Glu Leu Asp Gln Glu
            765                 770                 775

Glu Glu Glu Glu Asp Ser Pro Met Ile Ser Trp Gln Gly Val Leu Val
        780                 785                 790

Gly Tyr Gly Cys Gly Leu Val Ile Gly Leu Ser Val Ile Tyr Ile Met
    795                 800                 805

Trp Ser Thr Gln Tyr Pro Ala Trp Phe Ser Arg Met Asp Leu Lys Leu
810                 815                 820                 825

Glu His Ile Ile Thr Thr Lys Met Lys Lys His Lys Lys Arg Tyr
                830                 835                 840

(2) INFORMATION FOR SEQ ID NO: 3:

(i) SEQUENCE CHARACTERISTICS:
        (A) LENGTH: 177 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..177

(xi) SEQUENCE DESCRIPTION: SEQ ID NO: 3:

ATG GGA TTT GTT CTC TTT TCA CAA TTG CCT TCA TTT CTT CTT GTC TCT         48
Met Gly Phe Val Leu Phe Ser Gln Leu Pro Ser Phe Leu Leu Val Ser
 1               5                  10                  15

ACA CTT CTC TTA TTC CTA GTA ATA TCC CAC TCT TGC CGT GCC TAC TGT         96
Thr Leu Leu Leu Phe Leu Val Ile Ser His Ser Cys Arg Ala Tyr Cys
            20                  25                  30
```

```
AAC AGT TCT TGT ACA AGA GCT TTT GAC TGT CTT GGA CAA TGT GGA AGA        144
Asn Ser Ser Cys Thr Arg Ala Phe Asp Cys Leu Gly Gln Cys Gly Arg
         35                  40                  45

TGC GAC TTT CAT AAG CTT CAA TGT GTA CAT TGA                            177
Cys Asp Phe His Lys Leu Gln Cys Val His
 50                  55
```

(2) INFORMATION FOR SEQ ID NO: 4:

(i) SEQUENCE CHARACTERISTICS:
        (A) LENGTH: 2880 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

```
CATTTCTTGA TTTCTTCTCT ATCAACATAA CAAGTTTTGA TCATTTTTAG TGCAGAAATG        60

GATTGTGTAA AACTTGTATT CCTTATGCTA TATACCTTTC TCTGTCAACT TGCTTTATCC       120

TCATCCTTGC CTCATTTGTG CCCCGAAGAT CAAGCTCTTT CTCTTCTACA ATTCAAGAAC       180

ATGTTTACCA TTAATCCTAA TGCTTCTGAT TATTGTTACG ACATAAGAAC ATACGTAGAC       240

ATTCAGTCAT ATCCAAGAAC TCTTTCTTGG AACAAAAGCA CAAGTTGCTG CTCATGGGAT       300

GGCGTTCATT GTGACGAGAC GACAGGACAA GTGATTGCGC TTGACCTCCG TTGCAGCCAA       360

CTTCAAGGCA AGTTTCATTC CAATAGTAGC CTCTTTCAAC TCTCCAATCT CAAAAGGCTT       420

GATTTGTCTT TTAATAATTT CACTGGATCA CTCATTTCAC CAAAATTTGG TGAGTTTTCA       480

AATTTGACGC ATCTCGATTT GTCGCATTCT AGTTTTACAG GTCTAATTCC TTCTGAAATC       540

TGTCACCTTT CTAAACTACA CGTTCTTCGT ATATGTGATC AATATGGGCT TAGTCTTGTA       600

CCTTACAATT TGAACTGCT CCTTAAGAAC TTGACCCAAT TAAGAGAGCT CAACCTTGAA        660

TCTGTAAACA TCTCTTCCAC TATTCCTTCA AATTTCTCTT CTCATTTAAC AACTCTACAA       720

CTTTCAGGCA CAGAGTTACA TGGGATATTG CCCGAAAGAG TTTTTCACCT TTCCAACTTA       780

CAATCCCTTC ATTTATCAGT CAATCCCCAG CTCACGGTTA GGTTTCCCAC AACCAAATGG       840

AATAGCAGTG CATCACTCAT GACGTTATAC GTCGATAGTG TGAATATTGC TGATAGGATA       900

CCTAAATCAT TTAGCCATCT AACTTCACTT CATGAGTTGT ACATGGGTCG TTGTAATCTG       960

TCAGGGCCTA TTCCTAAACC TCTATGGAAT CTCACCAACA TAGTGTTTTT GCACCTTGGT      1020

GATAACCATC TTGAAGGACC AATTTCCCAT TTCACGATAT TTGAAAAGCT CAAGAGGTTA      1080

TCACTTGTAA ATAACAACTT TGATGGCGGA CTTGAGTTCT TATCCTTTAA CACCCAACTT      1140

GAACGGCTAG ATTTATCATC CAATTCCCTA ACTGGTCCAA TTCCATCCAA CATAAGCGGA      1200

CTTCAAAACC TAGAATGTCT CTACTTGTCA TCAAACCACT TGAATGGGAG TATACCTTCC      1260

TGGATATTCT CCCTTCCTTC ACTGGTTGAG TTAGACTTGA GCAATAACAC TTTCAGTGGA      1320

AAAATTCAAG AGTTCAAGTC CAAAACATTA AGTGCCGTTA CTCTAAAACA AAATAAGCTG      1380

AAAGGTCGTA TTCCGAATTC ACTCCTAAAC CAGAAGAACC TACAATTACT CTCCTTTCA       1440

CACAATAATA TCAGTGGACA TATTTCTTCA GCTATCTGCA ATCTGAAAAC ATTGATATTG      1500

TTAGACTTGG GAAGTAATAA TTTGGAGGGA ACAATCCCAC AATGCGTGGT TGAGAGGAAC      1560

GAATACCTTT CGCATTTGGA TTTGAGCAAA AACAGACTTA GTGGGACAAT CAATACAACT      1620

TTTAGTGTTG GAAACATTTT AAGGGTCATT AGCTTGCACG GGAATAAGCT AACGGGGAAA      1680

GTCCCACGAT CTATGATCAA TTGCAAGTAT TTGACACTAC TTGATCTAGG TAACAATATG      1740

TTGAATGACA CATTTCCAAA CTGGTTGGGA TACCTATTTC AATTGAAGAT TTAAGCTTG       1800
```

```
AGATCAAATA AGTTGCATGG TCCCATCAAA TCTTCAGGGA ATACAAACTT GTTTATGGGT    1860

CTTCAAATTC TTGATCTATC ATCTAATGGA TTTAGTGGGA ATTTACCCGA AAGAATTTTG    1920

GGGAATTTGC AAACCATGAA GGAAATTGAT GAGAGTACAG GATTCCCAGA GTATATTTCT    1980

GATCCATATG ATATTTATTA CAATTATTTG ACGACAATTT CTACAAAGGG ACAAGATTAT    2040

GATTCTGTTC GAATTTTGGA TTCTAACATG ATTATCAATC TCTCAAAGAA CAGATTTGAA    2100

GGTCATATTC CAAGCATTAT TGGAGATCTT GTTGGACTTC GTACGTTGAA CTTGTCTCAC    2160

AATGTCTTGG AAGGTCATAT ACCGGCATCA TTTCAAAATT TATCAGTACT CGAATCTTTG    2220

GATCTCTCAT CTAATAAAAT CAGCGGAGAA ATTCCGCAGC AGCTTGCATC CCTCACATTC    2280

CTTGAAGTCT TAAATCTCTC TCACAATCAT CTTGTTGGAT GCATCCCCAA AGGAAAACAA    2340

TTTGATTCGT TCGGGAACAC TTCGTACCAA GGGAATGATG GGTTACGCGG ATTTCCACTC    2400

TCAAAACTTT GTGGTGGTGA AGATCAAGTG ACAACTCCAG CTGAGCTAGA TCAAGAAGAG    2460

GAGGAAGAAG ATTCACCAAT GATCAGTTGG CAGGGGGTTC TCGTGGGTTA CGGTTGTGGA    2520

CTTGTTATTG GACTGTCCGT AATATACATA ATGTGGTCAA CTCAATATCC AGCATGGTTT    2580

TCGAGGATGG ATTTAAAGTT GGAACACATA ATTACTACGA AAATGAAAAA GCACAAGAAA    2640

AGATATTAGT GAGTAGCTAT ACCTCCAGGA TTCAAAGATT TCCGAGTTCC CAGTTGCTTG    2700

GGATGCAGAT AAAAGCCTTT TTATCTTTCA TAGTTTCTTA TCCTATGAAT AAAGATTTTA    2760

TTTTCATTTG TCTATGGCAC GTAGATATGT TCCGTCACTA AAAACATTGT ATTTCTCTCA    2820

ACTCTTTCGT CACATGATAT CAAAGAACAC TTGACTTCAA TTAAGTTAAA AAAAAAAAA     2880

(2) INFORMATION FOR SEQ ID NO: 5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other nucleic acid: DNA primer (xi) SEQUENCE DESCRIPTION: SEQ ID NO: 5:

GGAAGAGATG TTTACAGATT CAAGG                                           25

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other nucleic acid: DNA primer (xi) SEQUENCE DESCRIPTION: SEQ ID NO: 6:

ATCAGCAGGT CGATTCTTGT GG                                              22
```